(12) United States Patent
Fischer et al.

(10) Patent No.: US 7,186,829 B1
(45) Date of Patent: Mar. 6, 2007

(54) ARYL-SUBSTITUTED HETEROCYCLIC ENAMINONES

(75) Inventors: Reiner Fischer, Monheim (DE); Ralf Wischnat, Köln (DE); Jutta Böhmer, Köln (DE); Axel Trautwein, Bergisch Gladbach (DE); Jürgen Wiedemann, Leichlingen (DE); Udo Schneider, Leverkusen (DE); Hermann Hagemann, Leverkusen (DE); Mark Wilhelm Drewes, Langenfeld (DE); Peter Dahmen, Neuss (DE); Rolf Pontzen, Leichlingen (DE); Dieter Feucht, Monheim (DE); Christoph Erdelen, Leichlingen (DE); Peter Lösel, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 688 days.

(21) Appl. No.: 10/130,891

(22) PCT Filed: Nov. 21, 2000

(86) PCT No.: PCT/EP00/11838

§ 371 (c)(1),
(2), (4) Date: Sep. 11, 2002

(87) PCT Pub. No.: WO01/40202

PCT Pub. Date: Jun. 7, 2001

(30) Foreign Application Priority Data

Dec. 2, 1999 (DE) .................................. 199 58 164

(51) Int. Cl.
*C07D 265/30* (2006.01)
*C07D 295/00* (2006.01)
(52) U.S. Cl. .................................................. 544/106
(58) Field of Classification Search .................. 544/106
See application file for complete search history.

(56) References Cited

U.S. PATENT DOCUMENTS 3,865,863 A 2/1975 Field et al. ............. 260/465 E

FOREIGN PATENT DOCUMENTS

| EP | 04 902 20 | 6/1992 |
| EP | 05 629 36 | 9/1993 |
| EP | 08 429 31 | 5/1998 |
| WO | 00/27812 | 5/2000 |

OTHER PUBLICATIONS

Viossat B. Et Al.: "Structure du Benzoyl-1 n-Butyl-2 Phenacylidene-3 Tetrahydro-1,2,3,4 Quinoxaline" Acta Crystallographica. Section B, Structural Crystallography and Crystal Chemistry, Munksgaard, Copenhagen, DK, vol. B37, 1981, pp. 414-418, XP000984532 the whole document.

Trapani G. Et Al.: "Reaction of 2,2' -dithioaniline with 2-Alkyl-1, 3-diketones. Synthesis and chemical behaviour of some 2-acyl-2H-1, 4-benzothiazines" Journal Of Heterocyclic Chemistry, Heterocorporation. Provo, US, vol. 26, No. 3, May 1989-June 1989, pp. 721-724, XP000986352 Verbindung 17.

J. Pharm. Chem. (Engl. Trans.) Jul. 24, 1990, pp. 461-465, "Synthesis and Antibacterial Activity of 1, 2-Polymethylene-4-Quinolone-3-Carboxylic Acids" by R. G. Glushkov et al.

J. Pharm. Chem. (Engl. Transl.) 25, pp. 858-864, Dec. 1991, "Synthesis and Antitumor Activity of Pyrrolo [3,2-d] Pyrimidines" by M. V. Mezentseva et al.

Khim-Farm. Zh., 24, (month unavailable) 1990, pp. 24-27, R. G. Gluchkov et al, "Synthesis and Antibacterial Activity of 1,2-Polymethylene-4-Quinolone-3-CA".

Khim-Farm Zh., 25, (12), (month unavailable) 1992, pp. 19-23, M. V. Mezentseva et al, "Synthesis and Antitumor Activity of Pyrrolo [3,2-D] Pyrimidine Derivatives".

C. R. Acad. Sci., Ser. 11, Met. Phys. Chem., Aston 321, (12), (month unavailable) 1995, pp. 521-524, "Stereoselective annelation reactions starting from a cyclic β-enaminone: a-pyrrolidinylidenacetophenone" by V. Issartel et al.

Bull. Soc. Chim FR, (month unavailable) 1956, pp. 1210-1212, "No. 184,—Sur les morpholones-3. II.-Morpholones-3 N Substituées et dérivés," by Séguin et al.

J. Org. Chem., (month unavailable) 1981, 46, pp. 1221-1222, "Deuterium Isotope Effects in Carbon-13 Nuclear Magnetic Resonance Spectroscopy. Investigation of Tautomeric Equilibria in Enamino Ketone Systems" by G. M. Coppola et al.

J. Org. Chem., (month unavailable) 1980, 45, pp. 4198-4206, "Syntheses and Stereochemistry of Amidoximes" by D. F. Bushey and F. C. Hoover.

(Continued)

*Primary Examiner*—James O. Wilson
*Assistant Examiner*—Paul V. Ward
(74) *Attorney, Agent, or Firm*—Richard E. L. Henderson; Raymond J. Harmuth

(57) ABSTRACT

The invention relates to novel heterocyclic enaminones of the general formula (I)

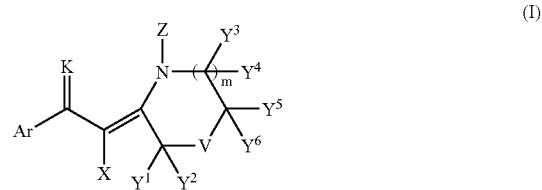

in which Ar, Z, K, X, $Y^1$, $Y^2$, $Y^3$, $Y^4$, $Y^5$, $Y^6$ and V are as defined in the description,
to their use as herbicides, acaricides and insecticides, and to processes for their preparation.

9 Claims, No Drawings

OTHER PUBLICATIONS

Helvetic Chimica Acta—vol. 54, Fasc. 2, (month unavailable) 1971, Nr. 69-70. pp. 710-734, "70, Sulfidkontraktion via alkylativ Kupplung: eine Methode zur Darstellung von β-Dicarbonylderivaten" by M. Roth et al.

Pharmazie, 51, (month unavailable) 1996, pp. 805-810, "Pyrrolidion enaminones structural related to gyrase inhibitors: synthesis, cyclization and pharmacological activity" by G. Dannhardt and A. Bauer.

Chem. Ber. 101, pp. 1979-1986, (month unavailable) 1968, "Umsetzung von Lactimäthem mit Dithiocarbazinsäureestern. Herstellung von 3-Mercapto-4.5-alkylen-1.2.4-triazolen" by J. Körösi et al.

J. Org. Chem., 55, (month unavailable) 1990, pp. 2246-2249, "A New Preparation of Difunctionalized Enamines from Thioamides Using Silver(I) Carbonate" by D. Brillon et al.

ARYL-SUBSTITUTED HETEROCYCLIC ENAMINONES

The invention relates to novel aryl-substituted heterocyclic enaminones, to a plurality of processes for their preparation, to intermediates, and to the use of the enaminones as crop protection agents, in particular as herbicides, acaricides, nematicides and insecticides.

Certain carbocyclic enaminones which are substituted in the phenyl ring have already been disclosed as intermediates for antibacterially active quinolones (R. G. Glushkov, N. B. Marchenko, A. N. Padeiskaya, L. D. Shipilova, Pharm. Chem. J. (Engl. Transl.) 24, 460–465, (1990)). Also known are carbocyclic enaminones which are unsubstituted in the phenyl ring (M. V. Mezentseva, A. V. Kadushkin, L. M. Alekseeva, A. S. Sokolova, V. G. Granik, Pharm. Chem. J. (Engl. Transl.) 25, 858–864 (1991); G. M. Coppola, R. Damon, A. D. Kahle, M. J. Shapiro, J. Org. Chem. 46, 1221–1222, (1981); D. Brillon, G. Sauvé, J. Org. Chem. 55, 2246–2249, (1990)). The use of these compounds as crop protection agents has hitherto not been described.

In a general manner, the novel heterocyclic enaminones are described by the formula (I)

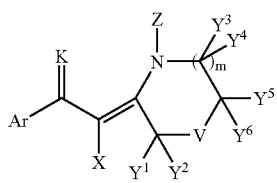

(I)

in which

K represents oxygen or sulphur,

Ar represents in each case substituted phenyl, naphthyl or represents in each case optionally substituted mono- or bicyclic hetaryl having 5 to 10 ring atoms, V represents oxygen or represents the groups —S(O)$_n$— or

W represents hydrogen, optionally substituted alkyl, alkenyl, alkinyl, cycloalkyl, cycloalkyl-alkyl, alkoxyalkyl, alkoxy, phenylalkyloxy, phenyl, phenylalkyl, hetaryl, hetarylalkyl or represents the groups —COR$^1$,

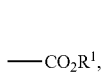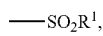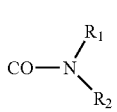

or cyano,

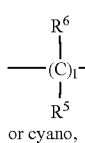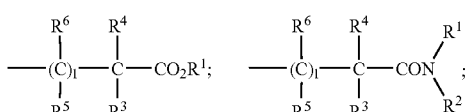

represents CN, 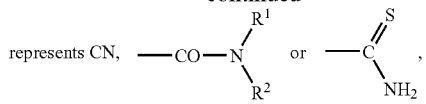

or cyano,

X represents CN,

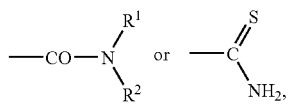

$Y^1$ and $Y^3$ independently of one another represent hydrogen, halogen or in each case optionally substituted alkyl, alkoxy, alkoxyalkyl, phenyl, phenylalkyl, hetaryl, hetarylalkyl or represent the groups

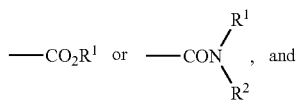, and $Y^2$, $Y^4$, $Y^6$ independently of one another represent hydrogen, halogen or optionally substituted alkyl, $Y^5$ represents hydrogen or in each case optionally substituted alkyl or phenyl, or $Y^4$ and $Y^5$ together with the carbon atoms to which they are attached represent an optionally substituted saturated or unsaturated cycle which is optionally interrupted by heteroatoms, or $Y^1$ and $Y^2$ together with the carbon atom to which they are attached represent an optionally substituted saturated or unsaturated cycle which is optionally interrupted by heteroatoms, Z represents hydrogen, represents in each case optionally substituted alkyl, alkenyl, alkinyl, cycloalkyl, cycloalkylalkyl, alkoxyalkyl, phenoxyalkyl, phenylalkyl-oxyalkyl, phenylthioalkyl, phenylalkyl-thioalkyl, phenyl, phenylalkyl, hetaryl, hetaryl-alkyl or represents the groups

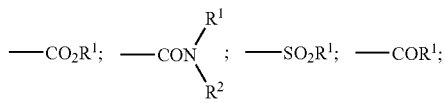
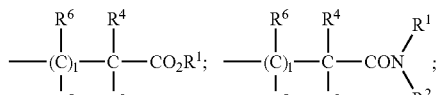
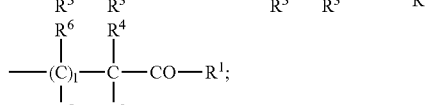

or cyano, l represents 0 to 3,
m represents 0 to 2,
n represents 0 to 2,
R$^1$ represents hydrogen, represents in each case optionally substituted, saturated or unsaturated alkyl or cycloalkyl, each of which is optionally interrupted by heteroatoms, represents in each case optionally substituted phenyl or hetaryl, represents in each case optionally substituted phenylalkyl or hetarylalkyl, $R^2$ represents hydrogen, represents in each case optionally substituted, saturated or unsaturated alkyl or alkoxy, represents in each case optionally substituted phenyl, phenylalkyl or phenylalkyloxy, $R^1$, $R^2$ furthermore together with the nitrogen atom to which they are attached may represent an optionally substituted cycle which is optionally interrupted by heteroatoms, or $R^3$ represents hydrogen, represents in each case optionally substituted alkyl or alkoxy, represents in each case optionally substituted phenyl or phenylalkyl, $R^4$ represents hydrogen or represents optionally substituted alkyl, and $R^5$, $R^6$ independently of one another represent hydrogen or represent optionally substituted alkyl.

For the compounds of the formula (I):

Ar preferably represents $Ar^1$, where $Ar^1$ represents phenyl, naphthyl or mono- or bicyclic hetaryl having five to ten ring atoms, each of which radicals is optionally mono- to pentasubstituted by halogen, $C_1$–$C_8$-alkyl, $C_2$–$C_8$-alkenyl, $C_2$–$C_8$-alkinyl, $C_1$–$C_8$-alkoxy, $C_2$–$C_8$-alkenyloxy, $C_3$–$C_8$-alkinyloxy, $C_1$–$C_8$-alkylthio, $C_1$–$C_6$-alkylsulphinyl, $C_1$–$C_6$-alkylsulphonyl, $C_1$–$C_6$-halogenoalkyl, $C_1$–$C_6$-halogeno-alkoxy, $C_2$–$C_8$-halogenoalkenyloxy, $C_1$–$C_2$-alkylidenediyl-dioxy, $C_1$–$C_2$-halogenoalkylidenediyl-dioxy, halogeno-$C_1$–$C_4$-alkylthio, halogeno-$C_1$–$C_4$-alkylsulphinyl, halogeno-$C_1$–$C_4$-alkylsulphonyl, hydroxyl, mercapto, nitro, cyano, amino or by the groups a) —L—CO—$R^7$,

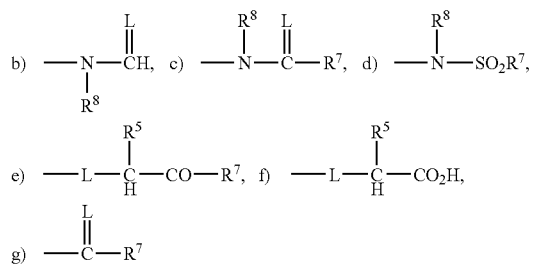

or represents $Ar^2$, where $Ar^2$ represents $Ar^1$ which is additionally substituted by phenyl, naphthyl, five- or six-membered hetaryl, phenyl-$C_1$–$C_4$-alkyl, phenyl-$C_1$–$C_4$-alkoxy, phenyl-$C_1$–$C_4$-alkyl-S(O)$_p$—, five- or six-membered hetaryl-$C_1$–$C_4$-alkoxy, five- or six-membered hetaryl-$C_1$–$C_4$-alkyl-S(O)$_p$—, phenoxy, phenyl-S(O)$_p$—, five- or six-membered hetaryloxy or hetaryl-S(O)$_p$—, where these substituents for their part are in each case optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

K preferably represents oxygen or sulphur.

L preferably represents oxygen or sulphur.

V preferably represents oxygen or represents the groups —S(O)$_n$— or

W preferably represents hydrogen, represents in each case optionally fluorine- and/or chlorine-substituted $C_1$–$C_8$-alkyl, $C_3$–$C_8$-alkenyl, $C_3$–$C_8$-alkinyl, $C_3$–$C_8$-cycloalkyl, $C_3$–$C_8$-cycloalkyl-$C_1$–$C_2$-alkyl, $C_1$–$C_6$-alkoxy, $C_1$–$C_4$-alkoxy-$C_2$–$C_4$-alkyl, represents phenyl, $C_1$–$C_4$-phenylalkyl, $C_1$–$C_4$-phenylalkyloxy, hetaryl, hetarylalkyl, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano or represents the groups

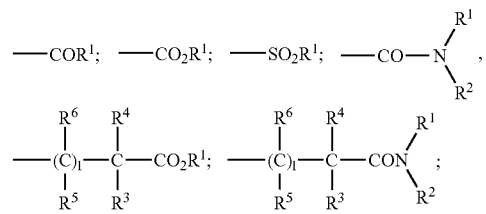

or cyano.

X preferably represents CN,

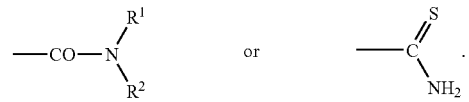

$Y^1$ and $Y^3$ independently of one another preferably represent hydrogen, halogen, $C_1$–$C_6$-alkyl, $C_1$–$C_4$-halogenoalkyl, $C_1$–$C_6$-alkoxy, $C_1$–$C_6$-alkoxy-$C_1$–$C_2$-alkyl, represent phenyl, phenyl-$C_1$–$C_4$-alkyl, five- or six-membered hetaryl or five- or six-membered hetaryl-$C_1$–$C_4$-alkyl, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro or represent the groups

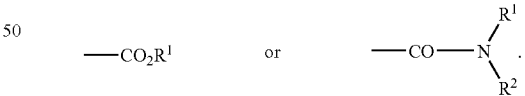

$Y^2$, $Y^4$, $Y^6$ independently of one another preferably represent hydrogen, halogen or represent fluorine- and/or chlorine-substituted $C_1$–$C_6$-alkyl.

$Y^5$ preferably represents hydrogen, represents optionally fluorine-substituted $C_1$–$C_6$-alkyl or represents phenyl which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$Y^4$ and $Y^5$ together with the carbon atoms to which they are attached preferably represent a 5- to 8-membered saturated or unsaturated cycle which may be interrupted by 1 to 3 heteroatoms from the group consisting of N, O, S and which may optionally be mono- to trisubstituted by halogen, $C_1$–$C_4$-alkyl, $C_1$–$C_4$-alkoxy, $C_1$–$C_4$-halogenoalkyl, $C_1$–$C_4$-halogenoalkoxy, cyano or nitro.

$Y^1$ and $Y^2$ together with the carbon atom to which they are attached preferably represent a $C_3$–$C_6$-cycloalkyl ring.

Z preferably represents hydrogen, represents in each case optionally fluorine- and/or chlorine-substituted $C_1$–$C_8$-alkyl, cyano-$C_1$–$C_6$-alkyl, $C_3$–$C_8$-alkenyl, $C_3$–$C_8$-alkinyl, $C_3$–$C_8$-cycloalkyl, $C_3$–$C_8$-cycloalkyl-$C_1$–$C_2$-alkyl, $C_1$–$C_4$-alkoxy-$C_1$–$C_4$-alkyl, $C_1$–$C_4$-halogenoalkoxy-$C_1$–$C_4$-alkyl, represents phenoxy-$C_1$–$C_4$-alkyl, phenyl-$C_1$–$C_4$-alkyloxy-$C_1$–$C_4$-alkyl, phenylthio-$C_1$–$C_4$-alkyl, phenyl-$C_1$–$C_4$-alkylthio-$C_1$–$C_4$-alkyl, phenyl, phenyl-$C_1$–$C_4$-alkyl, five- or six-membered hetaryl, five- or six-membered hetaryl-$C_1$–$C_4$-alkyl, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano or represents the groups

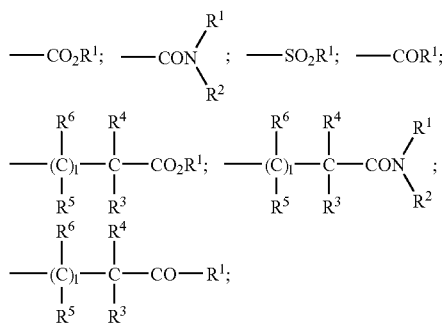

or cyano.

p preferably represents 0 to 2.

l preferably represents 0 to 2.

$R^1$ preferably represents hydrogen (but not in the radicals —$CO_2R_1$ and —$SO_2R^1$), represents in each case optionally fluorine- and/or chlorine-substituted $C_1$–$C_{10}$-alkyl, $C_2$–$C_{10}$-alkenyl, $C_3$–$C_6$-alkinyl, represents in each case optionally fluorine-, chlorine-, $C_1$–$C_4$-alkyl-, $C_1$–$C_4$-alkoxy-substituted $C_3$–$C_8$-cycloalkyl or $C_5$–$C_8$-cycloalkenyl, in which optionally one methylene group may be interrupted by oxygen or sulphur, or represents phenyl, pyridyl, thienyl, pyrimidyl, thiazolyl, phenyl-$C_1$–$C_4$-alkyl, pyridyl-$C_1$–$C_2$-alkyl, thiazolyl-$C_1$–$C_2$-alkyl, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$R^2$ preferably represents hydrogen, represents in each case optionally fluorine- and/or chlorine-substituted $C_1$–$C_6$-alkyl, $C_3$–$C_6$-alkenyl, $C_3$–$C_6$-alkinyl, $C_1$–$C_6$-alkoxy, $C_3$–$C_6$-alkenyloxy or represents phenyl, phenyl-$C_1$–$C_4$-alkyl or phenyl-$C_1$–$C_4$-alkoxy, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$R^1$, $R^2$ furthermore together with the nitrogen atom to which they are attached may preferably represent a five- to eight-membered cycle in which optionally one methylene group may be replaced by oxygen or sulphur and which may in each case optionally be substituted by $C_1$–$C_4$-alkyl.

$R^3$ preferably represents hydrogen, optionally halogen-substituted $C_1$–$C_6$-alkyl or represents phenyl or phenyl-$C_1$–$C_2$-alkyl, each of which is optionally mono- to tetra substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$R^4$ preferably represents hydrogen or $C_1$–$C_6$-alkyl.

$R^5$, $R^6$ preferably independently of one another represent hydrogen or optionally fluorine- and/or chlorine-substituted $C_1$–$C_4$-alkyl.

$R^7$ preferably represents in each case optionally fluorine- and/or chlorine-substituted $C_1$–$C_{10}$-alkyl, $C_2$–$C_{10}$-alkenyl, $C_3$–$C_{10}$-alkinyl, $C_1$–$C_{10}$-alkoxy, $C_1$–$C_4$-alkoxy-$C_1$–$C_4$-alkyl, $C_1$–$C_4$-alkylthio-$C_1$–$C_4$-alkyl, in each case optionally fluorine-, chlorine-, $C_1$–$C_4$-alkyl- and/or $C_1$–$C_4$-alkoxy-substituted $C_3$–$C_8$-cycloalkyl or $C_3$–$C_8$-cycloalkoxy, in which optionally one methylene group may be replaced by oxygen or sulphur, represents phenyl, phenoxy, benzyloxy, five- or six-membered hetaryl or phenyl-$C_1$–$C_4$-alkyl, each of which may optionally be mono- to tetrasubstituted by halogen, $C_1$–$C_6$-alkyl, $C_1$–$C_6$-alkoxy, $C_1$–$C_4$-halogeno-alkyl, $C_1$–$C_4$-halogenoalkoxy, cyano or nitro or, in the case of the radicals a) and c) mentioned under Ar, also represents a group

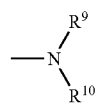

or, for the radical g), also represents hydroxyl.

$R^8$ preferably represents hydrogen or $C_1$–$C_4$-alkyl.

$R^9$ preferably represents hydrogen, in each case optionally fluorine- and/or chlorine-substituted $C_1$–$C_{10}$-alkyl, $C_3$–$C_8$-alkenyl, $C_3$–$C_8$-alkinyl, $C_1$–$C_{10}$-alkoxy, $C_3$–$C_8$-alkenyloxy, optionally fluorine-, chlorine-, $C_1$–$C_4$-alkyl- or $C_1$–$C_4$-alkoxy-substituted $C_3$–$C_8$-cycloalkyl, in which optionally one methylene group may be replaced by oxygen or sulphur, represents phenyl, phenyl-$C_1$–$C_4$-alkyl or phenyl-$C_1$–$C_2$-alkoxy, each of which may optionally be mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$R^{10}$ preferably represents hydrogen, $C_1$–$C_6$-alkyl or $C_3$–$C_6$-alkenyl.

$R^9$, $R^{10}$ furthermore together with the nitrogen atom to which they are attached may preferably represent an optionally $C_1$–$C_4$-alkyl-substituted five- to eight-membered cycle in which optionally one methylene group may be replaced by oxygen or sulphur.

m preferably represents 0 to 2.

n preferably represents 0 to 2.

K particularly preferably represents oxygen or sulphur.

Ar particularly preferably represents $Ar^1$, where $Ar^1$ represents phenyl, naphthyl, quinolinyl, thienyl, pyrimidyl, furanyl, thiazolyl, benzothiazolyl, oxazolyl, pyrazolyl or pyridyl, each of which is optionally mono- to trisubstituted by fluorine, chlorine, bromine, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_3$–$C_6$-alkinyloxy, $C_1$–$C_6$-alkylthio, $C_1$–$C_4$-alkylsulphinyl, $C_1$–$C_4$-alkylsulphonyl, $C_1$–$C_4$-halogenoalkyl, $C_1$–$C_4$-halogenoalkoxy, $C_2$–$C_4$-halogenoalkenyloxy, $C_1$–$C_2$-alkylidenediyl-dioxy, $C_1$–$C_2$-halogenoalkylidenediyl-dioxy, halogen-$C_1$–$C_2$-alkylthio, halogen-$C_1$–$C_2$-alkylsulphinyl, halogen- $C_1$–$C_2$-alkylsulphonyl, hydroxyl, mercapto, nitro, cyano, amino or by one of the following groups

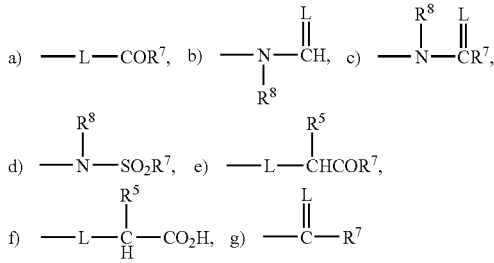

or particularly preferably represents $Ar^2$, where $Ar^2$ represents $Ar^1$ which is additionally substituted by phenyl, pyridyl, pyrimidyl, thienyl, furanyl, thiazolyl, tetrazolyl, triazolyl, benzyl, phenyl-$C_1$–$C_2$-alkoxy, phenyl-$C_1$–$C_2$-alkyl-$S(O)_p$—, thienyl-$C_1$–$C_2$-alkoxy, thiazolyl-$C_1$–$C_2$-alkoxy, pyridyl-$C_1$–$C_2$-alkoxy, pyrimidyl-$C_1$–$C_2$-alkoxy, thiazolyl-$C_1$–$C_2$-alkyl-$S(O)_p$—, pyridyl-$C_1$–$C_2$-alkyl-$S(O)_p$, phenoxy, phenyl-$S(O)_p$—, pyridyloxy, pyrimidyloxy, thiazolyloxy, pyridyl-$S(O)_p$—, pyrimidyl-$S(O)_p$— or thiazolyl-$S(O)_p$—, where these substituents for their part are optionally mono- to trisubstituted by fluorine, chlorine, bromine, $C_1$–$C_4$-alkyl, $C_2$–$C_4$-alkenyl, $C_1$–$C_4$-alkoxy, $C_1$–$C_2$-halogenoalkyl, $C_1$–$C_2$-halogenoalkoxy, nitro or cyano.

L particularly preferably represents oxygen or sulphur.

V particularly preferably represents oxygen or represents the groups —$S(O)_n$— or

W particularly preferably represents hydrogen, represents in each case optionally fluorine- and/or chlorine-substituted $C_1$–$C_6$-alkyl, $C_3$–$C_6$-alkenyl, $C_3$–$C_6$-alkinyl, $C_3$–$C_6$-cycloalkyl, $C_3$–$C_6$-cycloalkyl-$C_1$–$C_2$-alkyl, $C_1$–$C_4$-alkoxy, $C_1$–$C_4$-alkoxy-$C_2$–$C_3$-alkyl, represents phenyl, phenyl-$C_1$–$C_2$-alkyl, phenyl-$C_1$–$C_2$-alkoxy, pyridyl, thiazolyl, pyrimidyl, thienyl, pyridyl-$C_1$–$C_2$-alkyl, pyrimidyl-$C_1$–$C_2$-alkyl, thiazolyl-$C_1$–$C_2$-alkyl, each of which is optionally mono- to trisubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano or represents the groups

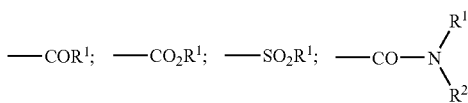

or cyano,

X particularly preferably represents CN,

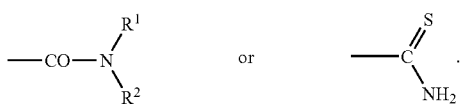

$Y^1$ and $Y^3$ independently of one another particularly preferably represent hydrogen, optionally represent fluorine, $C_1$–$C_4$-alkyl, $C_1$–$C_2$-halogenoalkyl, $C_1$–$C_4$-alkoxy, $C_1$–$C_4$-alkoxy-$C_1$–$C_2$-alkyl, represent phenyl, thienyl, pyridyl, thiazolyl, pyrimidyl, phenyl-$C_1$–$C_2$-alkyl, thiazolylmethyl, pyridylmethyl, each of which is optionally mono- to trisubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro or represent the groups

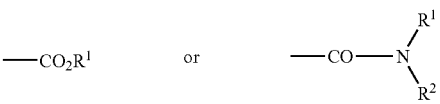

$Y^2$, $Y^4$, $Y^6$ independently of one another particularly preferably represent hydrogen or $C_1$–$C_4$-alkyl.

$Y^5$ particularly preferably represents hydrogen, represents optionally fluorine-substituted $C_1$–$C_4$-alkyl or represents phenyl which is optionally mono- to trisubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano.

$Y^4$ and $Y^5$ furthermore together with the carbon atoms to which they are attached particularly preferably represent a 5- or 6-membered saturated or unsaturated cycle which may be interrupted by a heteroatom from the group consisting of N, O, S and which may optionally be mono- or disubstituted by fluorine, chlorine, bromine, methyl, tert-butyl, methoxy, trifluoromethyl, trifluoromethoxy, cyano or nitro.

$Y^1$ and $Y^2$ together with the carbon atom to which they are attached particularly preferably represent a $C_4$–$C_6$-cycloalkyl ring.

Z particularly preferably represents hydrogen, represents in each case optionally fluorine- and/or chlorine-substituted $C_1$–$C_6$-alkyl, cyano-$C_1$–$C_3$-alkyl, $C_3$–$C_6$-alkenyl, $C_3$–$C_8$-alkinyl, $C_3$–$C_6$-cycloalkyl, $C_3$–$C_6$-cycloalkyl-$C_1$–$C_2$-alkyl, $C_1$–$C_4$-alkoxy-$C_1$–$C_2$-alkyl, $C_1$–$C_4$-halogeno-$C_1$–$C_2$-alkyl, represents phenoxy-$C_1$–$C_2$-alkyl, phenyl-$C_1$–$C_2$-alkyloxy-$C_1$–$C_2$-alkyl, phenylthio-$C_1$–$C_2$-alkyl, phenyl-$C_2$-alkylthio-$C_1$–$C_2$-alkyl, phenyl-$C_1$–$C_2$-alkyl, phenyl, pyridyl-$C_1$–$C_2$-alkyl, thiazolyl-$C_1$–$C_2$-alkyl, each of which is optionally mono- to trisubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano or represents the groups

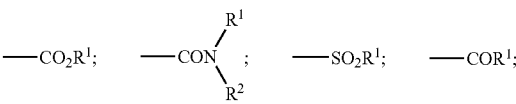

or cyano.

p particularly preferably represents 0 to 2.

$R^1$ particularly preferably represents hydrogen (but not in the radicals —$CO_2R^1$ and —$SO_2R^1$), represents in each case optionally fluorine- and/or chlorine-substituted $C_1$–$C_6$-alkyl, $C_3$–$C_6$-alkenyl, $C_3$–$C_4$-alkinyl, represents in each case optionally fluorine-, chlorine-, $C_1$–$C_2$-alkyl-, $C_1$–$C_2$-alkoxy-substituted $C_3$–$C_6$-cycloalkyl or represents phenyl or benzyl, each of which is optionally mono- or disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro.

$R^2$ particularly preferably represents hydrogen, represents in each case optionally fluorine- and/or chlorine-substituted $C_1$–$C_4$-alkyl, $C_3$–$C_4$-alkenyl, $C_3$–$C_4$-alkinyl, $C_1$–$C_4$-alkoxy, $C_3$–$C_4$-alkenyloxy or represents phenyl, benzyl, benzyloxy, each of which is optionally mono- or disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro.

$R^1$, $R^2$ furthermore together with the nitrogen atom to which they are attached may particularly preferably represent an optionally $C_1$–$C_2$-alkyl-substituted five- or six-membered cycle in which optionally one methylene group may be replaced by oxygen.

$R^5$ particularly preferably represents hydrogen, methyl or ethyl.

$R^7$ particularly preferably represents $C_1$–$C_6$-alkyl, $C_2$–$C_6$-alkenyl, $C_3$–$C_6$-alkinyl, $C_1$–$C_6$-alkoxy, $C_1$–$C_4$-alkoxy-$C_1$–$C_2$-alkyl, $C_1$–$C_4$-alkylthio-$C_1$–$C_2$-alkyl, each of which is optionally substituted by fluorine and/or chlorine, represents $C_3$–$C_6$-cycloalkyl or $C_3$–$C_6$-cycloalkoxy in which optionally one methylene group may be replaced by oxygen and which are in each case optionally substituted by fluorine, chlorine, $C_1$–$C_2$-alky and/or $C_1$–$C_2$-alkoxy, represents phenyl, phenoxy, benzyloxy, thienyl, furanyl, pyridyl, pyrimidyl, thiazolyl, pyrazolyl or phenyl-$C_1$–$C_2$-alkyl, each of which is optionally mono- or disubstituted by fluorine, chlorine, bromine, $C_1$–$C_4$-alkyl, $C_1$–$C_4$-alkoxy, trifluoromethyl, difluoromethoxy, trifluoromethoxy, cyano or nitro or, in the case of the radicals a) and c) mentioned under Ar, also represents a group

or, for the radical g), also represents hydroxyl.

$R^8$ particularly preferably represents hydrogen.

$R^9$ particularly preferably represents hydrogen, represents $C_1$–$C_6$-alkyl, $C_3$–$C_6$-alkenyl, $C_3$–$C_6$-alkinyl, $C_1$–$C_6$-alkoxy, $C_3$–$C_6$-cycloalkyl, in which optionally one methylene group may be replaced by oxygen and each of which is optionally substituted by fluorine and/or chlorine, represents phenyl or phenyl-$C_1$–$C_2$-alkyl, each of which is optionally mono- or disubstituted by fluorine, chlorine, bromine, $C_1$–$C_4$-alkyl, $C_1$–$C_4$-alkoxy, trifluoromethyl, difluoromethoxy, trifluoromethoxy, cyano or nitro.

$R^{10}$ particularly preferably represents hydrogen or $C_1$–$C_4$-alkyl.

$R^9$, $R_{10}$ furthermore together with the nitrogen atom to which they are attached may particularly preferably represent an optionally $C_1$–$C_2$-alkyl-substituted five- or six-membered cycle in which optionally one methylene group may be replaced by oxygen.

m particularly preferably represents 0 or 1.

n particularly preferably represents 0 to 2.

K very particularly preferably represents oxygen or sulphur.

Ar very particularly preferably represents $Ar^1$, where $Ar^1$ represents phenyl, thienyl, pyrimidyl, furanyl or pyridyl, each of which is optionally mono- to trisubstituted by fluorine, chlorine, bromine, methyl, ethyl, propyl, i-propyl, s-, n-, i- or t-butyl, methoxy, ethoxy, propoxy, i-propoxy, s-, n-, i- or t-butoxy, allyloxy, methallyloxy, 2-butenyloxy, propargyloxy, 2-butinyloxy, methylthio, ethylthio, methylsulphinyl, ethylsulphinyl, methylsulphonyl, ethylsulphonyl, trifluoromethyl, difluoromethoxy, trifluoromethoxy, methylenedioxy, difluoromethylenedioxy, tetrafluoroethylenedioxy, difluoromethylthio, trifluoromethylthio, trifluoromethylsulphinyl, trifluoromethylsulphonyl, hydroxyl, mercapto, nitro, cyano, amino, or by one of the following groups

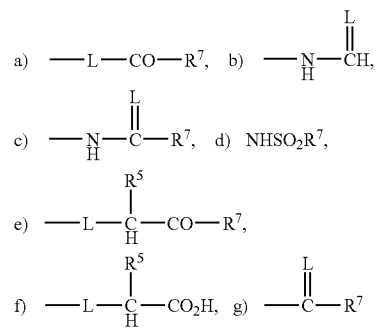

or represents $Ar^2$, where $Ar^2$ represents $Ar^1$ which is additionally substituted by phenyl, pyridyl, thienyl, tetrazolyl, triazolyl, benzyloxy, benzylthio, thiazolylmethyloxy, pyridylmethyloxy, pyrimidylmethyloxy, thiazolylmethylthio, pyridylmethylthio, phenoxy or phenylthio, where these substituents for their part are optionally mono- or disubstituted by fluorine, chlorine, bromine, methyl, ethyl, n- or i-propyl, s-, n-, i- or t-butyl, methoxy, ethoxy, i-propoxy, s-, n- or t-butoxy, trifluoromethyl, trifluoromethoxy, nitro or cyano.

L very particularly preferably represents oxygen or sulphur.

V very particularly preferably represents oxygen or sulphur.

X very particularly preferably represents

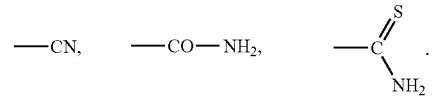

$Y^1$ and $Y^3$ independently of one another very particularly preferably represent hydrogen, methyl, ethyl, propyl, isopropyl, butyl, iso-butyl, sec-butyl, tertbutyl, represent phenyl or benzyl, each of which is optionally mono- to trisubstituted by fluorine, chlorine, bromine, methyl, methoxy, trifluoromethyl, difluoromethoxy or trifluoromethoxy.

$Y^2$, $Y^4$, $Y^6$ independently of one another very particularly preferably represent hydrogen, methyl or ethyl.

$Y^5$ very particularly preferably represents hydrogen, methyl, ethyl, propyl, i-propyl or represents phenyl which is optionally mono- or disubstituted by fluorine, chlorine, bromine, methyl, ethyl, i-propyl, tert-butyl, methoxy, ethoxy, i-propoxy, tert-butoxy, trifluoromethyl or trifluoromethoxy.

$Y^4$ and $Y^5$ furthermore together with the carbon atoms to which they are attached very particularly preferably represent a six-membered unsaturated cycle which may optionally be monosubstituted by fluorine, chlorine, bromine, methyl, methoxy, trifluoromethyl, trifluoromethoxy, cyano or nitro.

$Y^1$ and $Y^2$ furthermore together with the carbon atom to which they are attached very particularly preferably represent a cyclobutyl radical.

Z very particularly preferably represents hydrogen, methyl, ethyl, allyl, propargyl, cyclopropyl, cyclopentyl, cyclohexyl, cyclopropylmethyl, cyclopentylmethyl, cyclohexylmethyl, methoxymethyl, ethoxymethyl, represents phenyl, benzyl, pyridylmethyl, thiazolylmethyl, each of which is optionally mono- or disubstituted by fluorine, chlorine, bromine, methyl, methoxy, trifluoromethyl or trifluoromethoxy, cyano or nitro or represents the groups

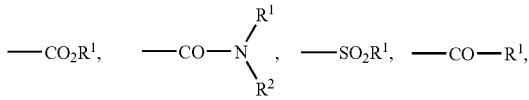

or cyano.

$R^1$ very particularly preferably represents hydrogen (but not in the radicals —$CO_2R^1$ and —$SO_2R^1$), methyl, ethyl, propyl, isopropyl, n-, s-, i- or t-butyl, allyl, propargyl, cyclopropyl, cyclopentyl, cyclohexyl, represents phenyl or benzyl, each of which is optionally mono- or disubstituted by fluorine, chlorine, bromine, methyl, methoxy, trifluoromethyl, trifluoromethoxy, cyano or nitro.

$R^2$ very particularly preferably represents hydrogen, methyl, ethyl, propyl, isopropyl, allyl, propargyl, methoxy, ethoxy, allyloxy or represents benzyloxy which is optionally mono- or disubstituted by fluorine, chlorine, bromine, methyl, methoxy, trifluoromethyl, trifluoromethoxy, cyano or nitro.

$R^1$, $R^2$ together with the nitrogen atom to which they are attached may very particularly preferably represent a pyrrolidine, thiazine, piperidine or morpholine radical.

$R^5$ very particularly preferably represents hydrogen, methyl or ethyl.

$R^7$ very particularly preferably represents methyl, ethyl, propyl, isopropyl, n-, s-, i- or t-butyl, vinyl, trifluoromethyl, methoxy, ethoxy, propoxy, isopropoxy, n-, s-, i- or t-butyloxy, cyclopropyl, cyclopentyl, cyclohexyl, cyclopentyloxy, cyclohexyloxy, represents phenyl, pyridyl or benzyl, each of which is optionally mono- or disubstituted by fluorine, chlorine, bromine, methyl, n-, s-, i- or t-butyl, methoxy, trifluoromethyl, trifluoromethoxy, cyano or nitro or, in the case of the radicals a) and c) mentioned under Ar, also represents a group

or, for the radical g), also represents hydroxyl.

$R^9$ very particularly preferably represents hydrogen, methyl, ethyl, propyl, isopropyl, n-, s-, i- or t-butyl, cyclopropyl, cyclopentyl, cyclohexyl, represents phenyl which is optionally mono- or disubstituted by fluorine, chlorine, bromine, methyl, methoxy, trifluoromethyl, trifluoromethoxy, cyano or nitro.

$R^{10}$ very particularly preferably represents hydrogen, methyl or ethyl.

$R^9$, $R^{10}$ together with the nitrogen atom to which they are attached very particularly preferably represent a pyrrolidine, piperidine or morpholine radical.

m very particularly preferably represents 1.

Ar especially preferably represents $Ar^1$, where $Ar^1$ represents phenyl, thienyl, pyrimidyl or pyridyl, each of which is optionally mono- to trisubstituted by fluorine, chlorine, bromine, methyl, ethyl, propyl, isopropyl, n-, s-, i- or t-butyl, methoxy, ethoxy, propoxy, isopropoxy, n-, s-, i- or t-butoxy, allyloxy, methallyloxy, 2-butenyloxy, propargyloxy, 2-butinyloxy, methylthio, ethylthio, methylsulphinyl, ethylsulphinyl, methylsulphonyl, ethylsulphonyl, trifluoromethyl, difluoromethoxy, trifluoromethoxy, methylenedioxy, difluoromethylenedioxy, tetrafluoroethylenedioxy, difluoromethylthio, trifluoromethylthio, trifluoromethylsulphinyl, trifluoromethylsulphonyl, hydroxyl, nitro, mercapto, cyano, amino or represents $Ar^2$, where $Ar^2$ represents $Ar^1$ which is additionally substituted by phenyl, benzyloxy or phenoxy, where these substituents for their part are optionally mono- or disubstituted by fluorine, chlorine, bromine, methyl, ethyl, isopropyl, n-, s-, i- or t-butyl, methoxy, ethoxy, isopropoxy, n-, s-, i- or t-butoxy, trifluoromethyl, trifluoromethoxy, nitro or cyano.

K especially preferably represents oxygen or sulphur.

V especially preferably represents oxygen or sulphur.

X especially preferably represents CN.

$Y^1$ and $Y^3$ independently of one another especially preferably represent hydrogen, methyl, ethyl or propyl.

Z especially preferably represents hydrogen or methyl.

m especially preferably represents 1.

$Y^2$, $Y^4$, $Y^5$, $Y^6$ independently of one another especially preferably represent hydrogen, methyl or ethyl.

All of the compounds of the formula (I) listed above can be present both as cis- and as trans-isomers. To simplify the presentation, in each case only one isomer was shown in the description of the compounds by formulae. However, the invention also refers to the respective other isomers.

The abovementioned general or preferred radical definitions apply both to the end products of the formula (I) and, correspondingly, to the starting materials and intermediates required in each case for the preparation. These radical definitions can be combined with one another as desired, i.e. including combinations between the given preferred ranges.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Special preference according to the invention is given to the compounds of the formula (I) which contain a combination of the meanings listed above as being especially preferred.

Saturated or unsaturated hydrocarbon radicals, such as alkyl or alkenyl, can in each case be straight-chain or branched, as far as this is possible, including in combination with heteroatoms, such as, for example, in alkoxy.

Unless stated otherwise, optionally substituted radicals can be mono- or polysubstituted, and in the case of polysubstitutions, the substituents can be identical or different.

It has been found that the novel compounds of the formula (I) are obtained by the process described below:

(A) compounds of the formula (I),

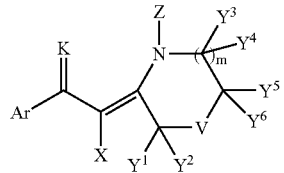

in which
Ar, V, X, $Y^1$, $Y^2$, $Y^3$, $Y^4$, $Y^5$, $Y^6$ and m are as defined above and
K represents oxygen and
Z represents hydrogen,
are obtained when
compounds of the formula (II),

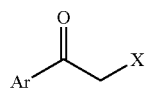

in which
Ar and X are as defined above,
are reacted with compounds of the formula (III),

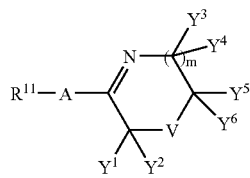

in which
V, $Y^1$, $Y^2$, $Y^3$, $Y^4$, $Y^5$, $Y^6$ and m are as defined above and
A represents O or $S(O)_q$, where q represents 0 or 2, and
$R^{11}$ represents alkyl, in particular $C_1$–$C_6$-alkyl, or benzyl, if appropriate in the presence of a diluent and if appropriate in the presence of a base or an acid and/or a metal compound of the formula (IIIa),

 Me(Q)$_2$ (IIIa)

in which
Me represents a divalent transition metal atom, in particular nickel, and
Q represents a chelate ligand, in particular a bidentate chelate ligand, such as, for example, acetylacetonate (R. G. Glushkov et al., Khim.-Farm. Zh. 24, (7), (1990), 24–27; M. V. Mezentseva et al., Khim.-Farm. Zh. 25, (12), (1991), 19–23; G. Dannhardt, A. Bauer, Pharmazie 51,(1996), 805–810).

(B) Moreover, it has been found that compounds of the formula (I)

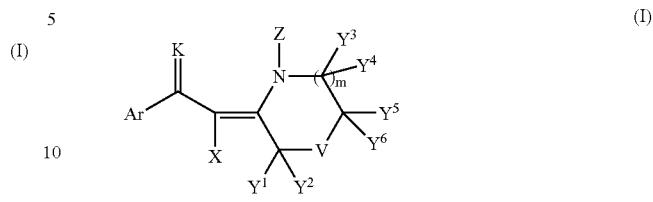

in which
Ar, V, $Y^1$, $Y^2$, $Y^3$, $Y^4$, $Y^5$, $Y^6$, X and m are as defined above and
K represents oxygen and
Z represents hydrogen
are obtained when compounds of the formula (IV),

in which
Ar and X are as defined above and
Hal represents halogen, in particular chlorine or bromine,
are reacted with compounds of the formula (V),

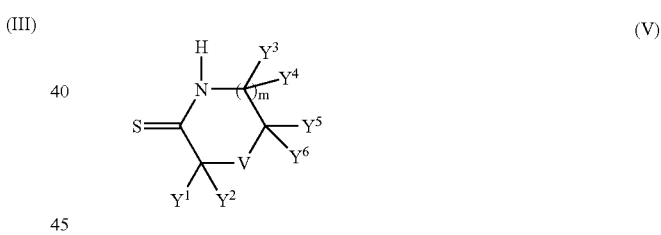

in which
V, $Y^1$, $Y^2$, $Y^3$, $Y^4$, $Y^5$, $Y^6$ and m are as defined above,
if appropriate in the presence of a diluent, to give compounds of the formula (VI),

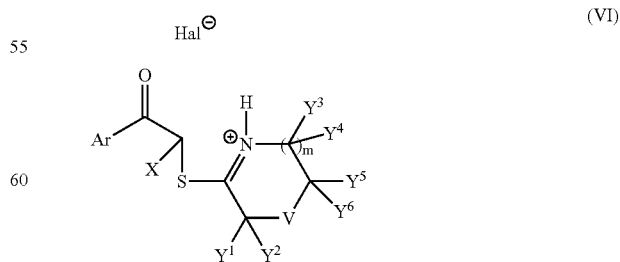

in which
V, Ar, X, $Y^1$, $Y^2$, $Y^3$, $Y^4$, $Y^5$, $Y^6$ and m are as defined above, which are reacted further, if appropriate in the presence of a base and if appropriate in the presence of a trivalent phosphorus compound (for example triphenylphosphine, triethyl phosphite), with elimination of sulphur and hydrogen halide, to give compounds of the formula (I)

in which
Ar, V, X, $Y^1$, $Y^2$, $Y^3$, $Y^4$, $Y^5$, $Y^6$ and m are as defined above and
K represents oxygen and
Z represents hydrogen (see A. Eschenmoser et al., Helv. Chim. Acta 54, (1971), 710–734; V. Issartel et al., C. R. Acad. Sci., Ser. II, Mec., Phys., Chim., Astron. 321, (12), (1995), 521–524).

(C) Furthermore, it has been found that compounds of the formula (I)

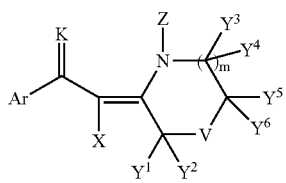

(I)

in which
Ar, V, Z, X, $Y^1$, $Y^2$, $Y^3$, $Y^4$, $Y^5$, $Y^6$ and m and n have one of the meanings defined above and
K represents oxygen, but
Z does not represent hydrogen are obtained when compounds of the formula (VII),

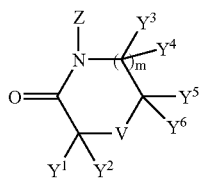

(VII)

in which
V, Z, $Y^1$, $Y^2$, $Y^3$, $Y^4$, $Y^5$, $Y^6$ and m have one of the meanings given above and Z does not represent hydrogen, are reacted with halogenating agents, such as, for example, phosgene, diphosgene and triphosgene, if appropriate in the presence of a diluent, to give compounds of the formula (VIII),

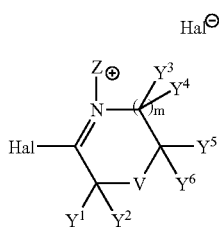

(VIII)

in which
V, Z, $Y^1$, $Y^2$, $Y^3$, $Y^4$, $Y^5$, $Y^6$ and m have one of the meanings given above
and Z does not represent hydrogen and
Hal represents halogen, in particular chlorine or bromine, which are then reacted with compounds of the formula (II)

(II)

in which
Ar, X are as defined above, if appropriate in the presence of a diluent and if appropriate in the presence of an acid acceptor (see G. Dannhardt, A. Bauer, Pharmazie 51, (1996), 805–810).

(D) Furthermore, it has been found that compounds of the formula (I),

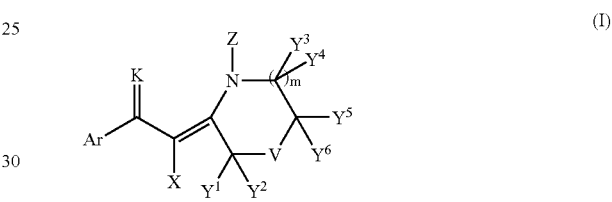

(I)

in which
Ar, V, Z, X, $Y^1$, $Y^2$, $Y^3$, $Y^4$, $Y^5$, $Y^6$ and m have one of the meanings given above and
K represents oxygen, but
Z does not represent hydrogen
are obtained when compounds of the formula (Ia),

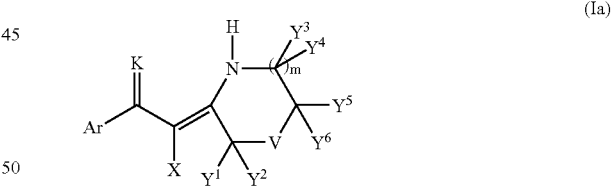

(Ia)

in which
Ar, V, X, $Y^1$, $Y^2$, $Y^3$, $Y^4$, $Y^5$, $Y^6$ and m are as defined above,
K represents oxygen, are reacted with alkylating agents, acylating agents, sulphonylating agents or condensing agents of the formula (IX),

Z-G (IX)

in which
G is a leaving group, such as halogen (in particular iodine, bromine, chlorine), sulphonate (such as, for example, mesylate, triflate or toluenesulphonate) or alkoxy, if appropriate in the presence of a solvent and if appropriate in the presence of a base.

(E) Moreover, it has been found that compounds of the formula (I²),

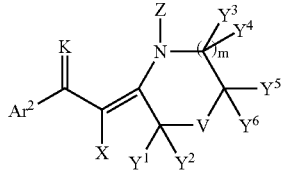

(I²)

in which
Ar², V, X, Y¹, Y², Y³, Y⁴, Y⁵, Y⁶, Z and m are as defined above and
K represents oxygen, are obtained when compounds of the formula (I¹),

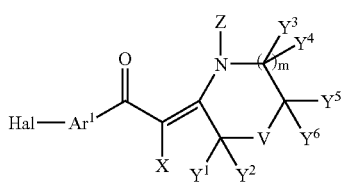

(I¹)

in which
Ar¹, V, X, Y¹, Y², Y³, Y⁴, Y⁶, Z and m are as defined above and
Hal represents halogen, in particular bromine, are reacted with boronic acids of the formula (X),

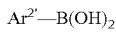

(X)

in which
Ar²′ represents the substituents which are mentioned above under Ar² as additional substituents for Ar¹, in the presence of a solvent, if appropriate in the presence of a base and a noble metal complex, preferably a palladium complex.

(F) Furthermore, it has been found that compounds of the formula (I),

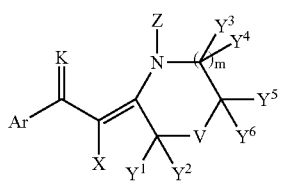

(I)

in which
Ar, Z, V, X, Y¹, Y², Y³, Y⁴, Y⁵, Y⁶ and m are as defined above and
K represents sulphur, are obtained when compounds of the formula (I),

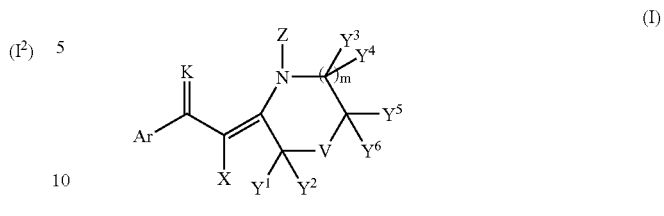

(I)

in which
Ar, Z, V, X, Y¹, Y², Y³, Y⁴, Y⁵, Y⁶ and m are as defined above and
K represents oxygen, are reacted in the presence of a sulphurizing reagent, such as, for example, phosphorus pentasulphide or 2,4-bis-(4-methoxyphenyl)-1,2,3,4-dithiaphosphetane-2,4-disulphide (Lawesson's Reagent) in the presence of a solvent.

(G) Furthermore, it has been found that compounds of the formula (I³),

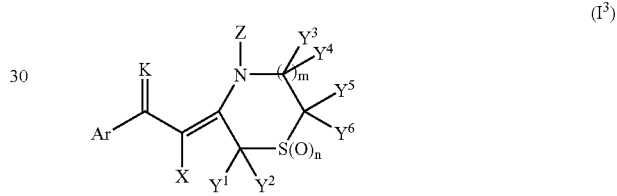

(I³)

in which
Ar, K, X, Z, Y¹, Y², Y³, Y⁴, Y⁵, Y⁶ and m are as defined above and
n represents the number 1 or 2, are obtained when compounds of the formula (I)

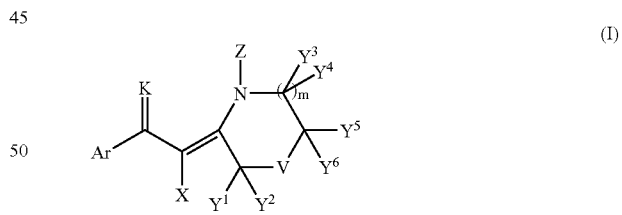

(I)

in which
Ar, K, Z, X, Y¹, Y², Y³, Y⁴, Y⁵, Y⁶ and m are as defined above and
V represents a sulphur atom, are oxidized in the presence of peracids (such as, for example, peracetic acid or m-chloroperbenzoic acid) or hydrogen peroxide in the presence of molybdates or tungstates (such as, for example, ammonium molybdate or sodium tungstate).

Using according to process A, for example, 4-methylbenzoylacetonitrile and 2-methoxy-2-dihydro-morpholine as starting materials, the course of the reaction can be represented by the following equation:

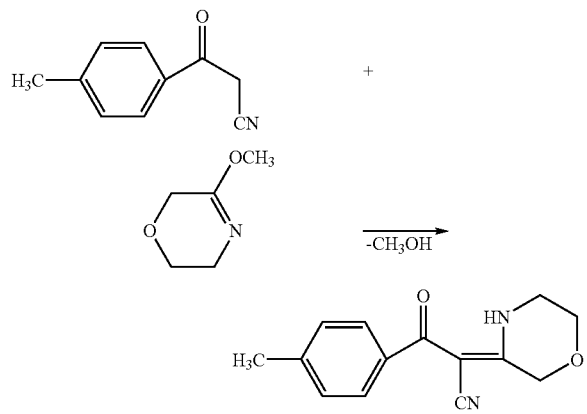

Using according to process B, for example, 2-bromo-2-(3-chlorobenzoyl)acetonitrile and morpholine-3-thione as starting materials, the course of the reaction can be represented by the following equation:

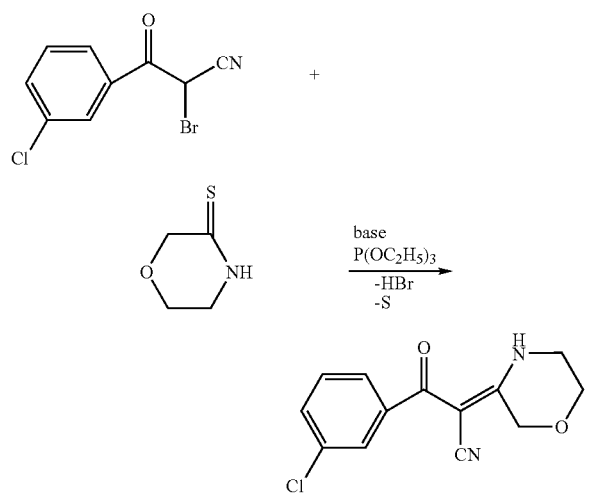

Using according to process C, for example, 3,4-dichlorobenzoyl-acetonitrile and N-methyl-morpholin-3-one as starting materials, the course of the reaction can be represented by the following equation:

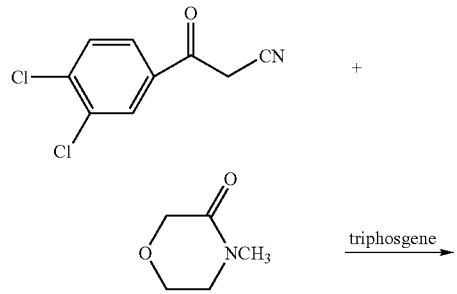

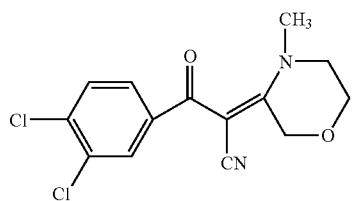

Using according to process D, for example, 3-(4-trifluoromethoxy-phenyl)-2-(1,4-oxazinan-3-ylidene)-3-oxo-propionitrile and 2-chloro-5-chloromethyl-pyridine as starting materials, the course of the reaction can be represented by the following equation:

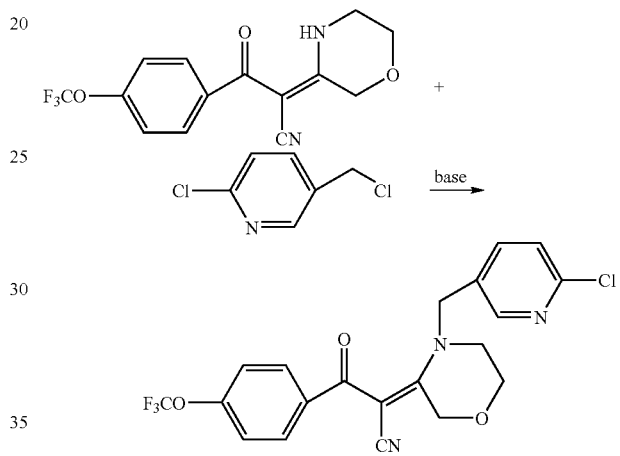

Using according to process D, for example, 3-(4-trifluoromethyl-phenyl)-2-(1,4-oxazinan-3-ylidene)-3-oxo-propionitrile and 4-chlorobenzoyl chloride as starting materials, the course of the reaction can be represented by the following equation:

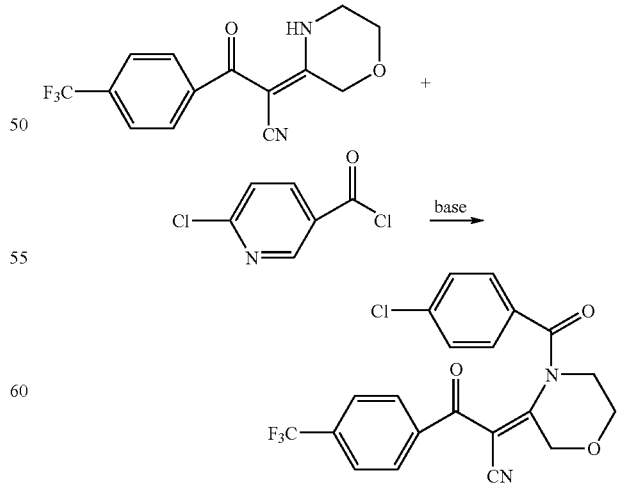

Using according to process E, for example, 3-(4-bromophenyl)-2-(1,4-oxazinan-3-ylidene)-3-oxo-propionitrile and 4-chloro-phenylboronic acid as starting materials, the course of the reaction can be represented by the following equation:

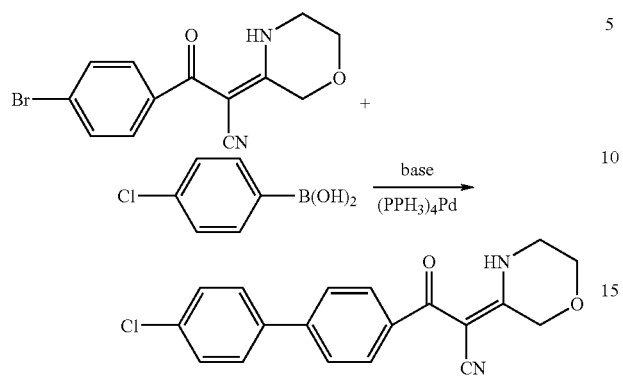

Using according to process F, for example, 3-(4-chlorophenyl)-2-(1,4-oxazinan-3-ylidene)-3-oxo-propionitrile and Lawesson's Reagent as starting materials, the course of the reaction can be represented by the following equation

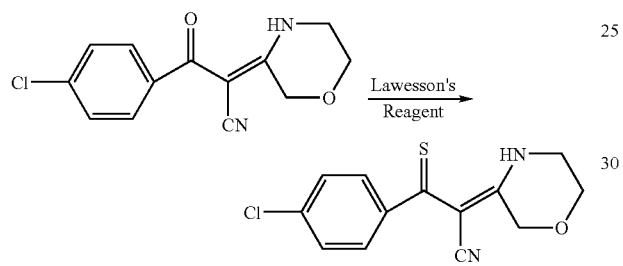

Using according to process G, for example, 3-(3,4-dichlorophenyl)-2-(1,4-thioxazinan-3-ylidene)-3-oxo-propionitrile and two equivalents of m-chloroperbenzoic acid (MCPBA) as starting materials, the course can be represented by the following equation:

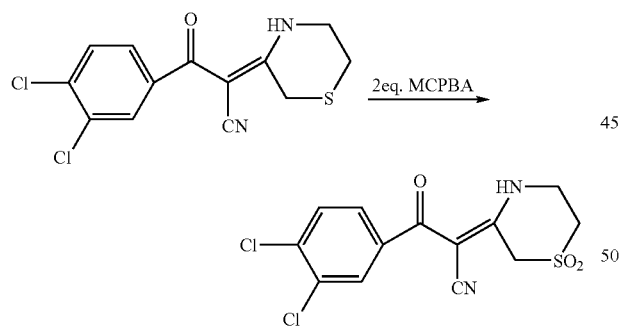

Some of the compounds, required as starting materials in process (A), of the formula (II),

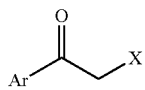

(II)

in which
Ar, X are as defined above,
are novel and can be prepared by processes known in principle from the literature (Organikum, 16$^{th}$ revised edition, pp. 415, 417, VEB Deutscher Verlag der Wissenschaften, Berlin 1986).

Among the compounds of the formula (II), the compounds of the formula (II-1-b),

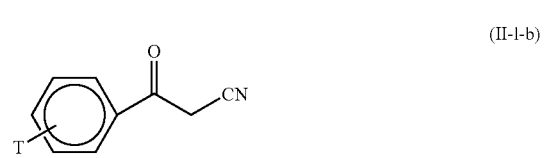

(II-1-b)

where

| Comp. No. | T | m.p. ° C. |
|---|---|---|
| II-1-b-1 | 3-Cl, 4-F | 78 |
| II-1-b-2 | 4-Cl, 3-F | 87 |
| II-1-b-3 | 3,5-(CF$_3$)$_2$ | 91 |
| II-1-b-4 | 2,4-Cl$_2$, 5-F | 106 |
| II-1-b-5 | 3,5-Cl$_2$, 4-F | 138–140 |
| II-1-b-6 | 4-Cl, 2-F | 90–94 |
| II-1-b-7 | 3-CF$_3$, 5-CH$_3$ | 92 |
| II-1-b-8 | 3-Cl, 4,5-F$_2$ | 84–88 |
| II-1-b-9 | 4-CN, 2,5-F$_2$ | 107–108 |
| II-1-b-10 | 2,3-F$_2$ | 74 |
| II-1-b-11 | 3-F, 4-CF$_3$ | 92 |
| II-1-b-12 | 3,4-O—CF$_2$—O | 70–73 |
| II-1-b-13 | 3-NO$_2$, 5-CF$_3$ | |
| II-1-b-14 | 4-Cl, 2,5-F$_2$ | 116 |
| II-1-b-15 | 3,4,5-(OC$_2$H$_5$)$_3$ | 122 |
| II-1-b-16 | 4-Br, 2-F | 118 |
| II-1-b-17 | 2,6-Cl$_2$, 4-CF$_3$ | 123 |
| II-1-b-18 | 2-F, 4-NO$_2$ | 168 |
| II-1-b-19 | 2,4-Cl$_2$, 5-NO$_2$ | 100 |
| II-1-b-20 | 4-Cl, 2-F, 5-NO$_2$ | 118 |
| II-1-b-21 | 2,4-F$_2$, 5-NO$_2$ | 128 |
| II-1-b-22 | 4-Br, 2-F, 5-NO$_2$ | 141 |
| II-1-b-23 | 2-F, 4-CF$_3$ | 62 |
| II-1-b-24 | 4-OCF$_3$, 3-NO$_2$ | 95 |
| II-1-b-25 | 4-Cl, 2-NO$_2$ | 130 |
| II-1-b-26 | 2-F, 3-CF$_3$ | 67–69 |
| II-1-b-27 | 2-Cl, 6-F | 46–48 |
| II-1-b-28 | 2-Cl, 3-CF$_3$ | 90–93 |
| II-1-b-29 | 3,4-O—(CF$_2$)$_2$—O— | 206 |
| II-1-b-30 | 2-Cl, 4-SCH$_3$ | 110 |
| II-1-b-31 | 2-Cl, 4-SO$_2$CH$_3$ | 202 | and the compound of the formula (II-2-b),

(II-2-b)

| Comp. No. | T | m.p. ° C. |
|---|---|---|
| II-2-b-1 | 2,6-Cl$_2$ | >220 |
| II-2-b-2 | 2,6-Cl$_2$, 4-CH$_3$ | 95 |
| II-2-b-3 | 6-Cl | 122 | and the compound of the formula (II-3-b), (II-3-b)

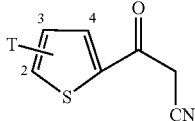

| Comp. No. | T | m.p. ° C. |
|---|---|---|
| II-3-b-1 | 2-CF$_3$, 3-(4-Cl'—C$_6$H$_4$) | oil |
| II-3-b-2 | 2-CF$_3$, 3-(2,4-Cl$_2$'—C$_6$H$_3$) | oil | and the compound No. II-4-b-1

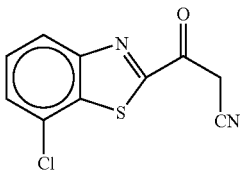

Comp. No. II-4-b-1;m.p.241° C.

and the compound No. II-5-b-1

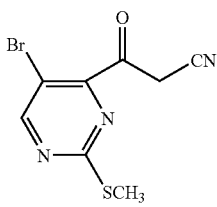

Comp. No. II-5-b-1, resin are particularly suitable for preparing novel pesticidal, in particular acaricidal, herbicidal and insecticidal, end products. The compounds of the formulae II-1-b to II-5-b form part of the subject-matter of an earlier, but not yet published, patent application.

The compounds of the formula (II) are obtained, for example, by hydrolyzing compounds of the formula (XI), (XI)

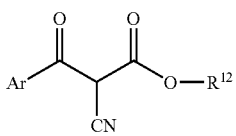

in which
Ar is as defined above,
R$^{12}$ represents alkyl, in particular C$_1$–C$_6$-alkyl, or benzyl, which may optionally be substituted,
in the presence of an acid (for example an inorganic acid, such as hydrochloric acid) or a base (for example an alkali metal hydroxide, such as sodium hydroxide or potassium hydroxide) and, if appropriate, a diluent (for example an aqueous alcohol, such as methanol or ethanol) at temperatures between 0° C. and 200° C., preferably between 20° C. and 150° C., followed by decarboxylation.

The compounds of the formula (XI) can be prepared by known processes (Organikum, 16$^{th}$ revised edition, pp. 480, VEB Deutscher Verlag der Wissenschaften, Berlin 1986).

The compounds of the formula (XI) are obtained, for example, by reacting compounds of the formula (XII), (XII)

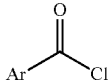

in which
Ar is as defined above,
with cyanoacetic esters of the formula (XIII), (XIII)

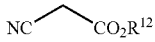

in which
R$^{12}$ represents alkyl, in particular C$_1$–C$_6$-alkyl,
in the presence of a base (for example a metal alkoxide, such as sodium methoxide or sodium ethoxide) and, if appropriate, in the presence of a diluent (for example ether or the alcohol derived from the alkoxide) at temperatures of from 0° C. to 150° C., preferably between 20° C. and 120° C.

Some of the compounds of the formula (XII) are novel and can be prepared by processes known in principle (for example Organikum, 16$^{th}$ revised edition, p. 423, VEB Deutscher Verlag der Wissenschaften, Berlin 1986).

The compounds of the formula (XII) are obtained, for example, by reacting compounds of the formula (XIV), (XIV)

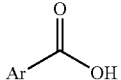

in which
Ar is as defined above,
with halogenating agents (for example thionyl chloride, phosgene, phosphorus trichloride), if appropriate in the presence of a diluent (for example optionally chlorinated aliphatic or aromatic hydrocarbons, such as toluene or methylene chloride) at temperatures from 0° C. to 150° C., preferably between 20° C. and 100° C.

Cyanoacetic esters of the formula (XIII) are known compounds of organic chemistry.

The compounds, also required as starting materials in process (A), of the formula (III), (III)

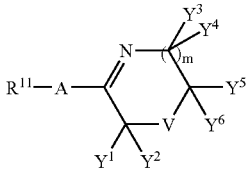

in which
V, Y$^1$, Y$^2$, Y$^3$, Y$^4$, Y$^5$, Y$^6$, R$^{11}$ and m are as defined above and
A represents oxygen,
can be prepared by known processes (J. Körösi, P. Berensci, Chem. Ber., 101, 1979 (1968)).

The compounds of the formula (III) are obtained, for example, by reacting compounds of the formula (VII),

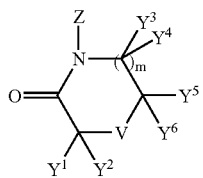
(VII)

in which

V, Y$^1$, Y$^2$, Y$^3$, Y$^4$, Y$^5$, Y$^6$ and m are as defined above and

Z represents hydrogen, with alkylating agents (for example dimethyl sulphate, triethyloxonium tetrafluoroborate (Meerwein salt)) at temperatures of from −20° C. to 150° C., preferably from 0° C. to 100° C.

Furthermore, the compounds, required as starting materials in process A, of the formula (III),

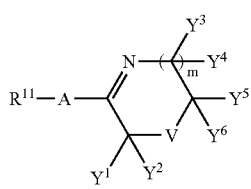
(III)

in which

V, Y$^1$, Y$^2$, Y$^3$, Y$^4$, Y$^5$, Y$^6$, R$^{11}$ and m are as defined above and A represents sulphur, are obtained when compounds of the formula (VII),

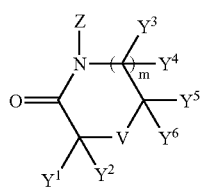
(VII)

in which

V, Z, Y$^1$, Y$^2$, Y$^3$, Y$^4$, Y$^5$, Y$^6$ and m are as defined above and

Z represents hydrogen, are initially converted with a sulphurizing agent, for example Lawesson's Reagent, into the thioamide of the formula (V),

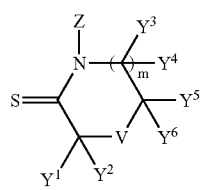
(V)

in which

V, Y$^1$, Y$^2$, Y$^3$, Y$^4$, Y$^5$, Y$^6$ and m are as defined above, in the presence of a solvent, followed by reaction with an alkylating agent of the formula (XV), R$^{11}$—Hal (XV)

in which

R$^{11}$ is as defined above and

Hal represents halogen, in particular iodine and bromine, if appropriate in the presence of a base and in the presence of a solvent.

The process (A) is characterized in that compounds of the formula (II), in which Ar, X are as defined above, and compounds of the formula (III), in which R$^{11}$, V, W, Y$^1$, Y$^2$, Y$^3$, Y$^4$, Y$^5$, Y$^6$ and m are as defined above, are reacted with one another in the presence of a diluent and if appropriate in the presence of a base.

Suitable diluents for the process (A) are all organic solvents which are inert to the reaction participants. Preference is given to using optionally chlorinated aliphatic or aromatic hydrocarbons, such as toluene, xylene, 1,2-dichlorobenzene, chloroform or methylene chloride, furthermore polar solvents, such as dimethyl sulphoxide, di methyl formamide, dimethylacetamide or N-methylpyrrolidone.

Solvents which can also be used are ethers, such as, for example, diethyl ether, methyl tert-butyl ether, tetrahydrofuran or dioxane, and also nitrites, such as, for example, acetonitrile, and esters, such as, for example, ethyl acetate, furthermore also ketones, such as acetone or isopropyl methyl ketone.

Suitable bases for carrying out process (A) are all customary acid acceptors which do not hydrolyze the reaction participants.

Preference is given to using tertiary amines, such as diazabicyclooctane (DABCO), diazabicycloundecene (DBU), diazabicyclononene (DBN), triethylamine, pyridine or N,N-dimethylaniline.

It is also possible to use alkoxides, such as sodium methoxide, sodium ethoxide, magnesium ethoxide, potassium tert-butoxide, and metal hydrides, such as sodium hydride, calcium hydride, and also alkali metal or alkaline earth metal carbonates or bicarbonates, such as sodium bicarbonate, potassium carbonate or sodium carbonate.

Suitable acids for carrying out process (A) are all acids which do not hydrolyze the reaction participants. Preference is given to using organic acids, such as p-toluenesulphonic acid and trifluoroacetic acid.

When carrying out the process (A), the reaction temperature can be varied within a relatively wide range. Advantageously, the reaction is carried out at temperatures between −20° C. and 160° C., preferably between 0° C. and 120° C.

The process (A) is preferably carried out under atmospheric pressure.

When carrying out the process (A), the reaction component of the formula (m) is employed in an equimolar amount or in a relatively large excess (up to 5 mol), preferably in 1.5 to 2 times the molar amount, based on the reaction component of the formula (II).

The base, which is used if appropriate, is preferably employed in an equimolar amount to the reaction component of the formula (II). The acid, which is used if appropriate, is preferably employed in catalytic amounts.

The process (B) is characterized in that compounds of the formula (IV) are in each case reacted with thioamides of the formula (V), if appropriate in the presence of a diluent and if appropriate in the presence of an acid binder.

The starting materials of the formula (IV) can be prepared by known processes (Sequin, Vieles, BSCFAS, Bull. Soc. Chim. Fr. (1956) 1210, 1211; Bushey, Hoover, J. Org. Chem. 45, 4198, (1980)). The compounds of the formula (V) can be prepared in inert solvents, such as, for example, toluene, from the corresponding keto compound, by using thionylating agents, in particular $P_2S_5$ and Lawesson's Reagent (see Preparation Example 4).

Suitable diluents for the process (B) according to the invention are all solvents which are inert to the compounds of the formula (IV). Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethylformamide, N-methylpyrrolidone, dimethyl sulphoxide and sulpholane.

Suitable acid binders for the reaction according to the process (B) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, polymeric bases, such as diisopropylaminopolystyrene, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable phosphorus reagents for the process (B) according to the invention are alkyl phosphites, such as triethyl phosphite, tributyl phosphite, or triphenylphosphines, such as triphenylphosphine.

The reaction temperature in the process (B) according to the invention can be varied within a relatively wide range. In general, the reaction is carried out at temperatures between 0° C. and 200° C., preferably between −20° C. and 150° C.

For carrying out the process (B) according to the invention, the starting materials of the formula (IV) and the thioamide of the formula (V) are generally each employed in approximately equivalent amounts. However, it is also possible to use a relatively large excess of one or the other component. Work-up is carried out by customary methods.

The process (C) is characterized in that compounds of the formula (VII) are reacted with halogenating agents, such as, for example, phosgene, diphosgene, triphosgene, if appropriate in the presence of a diluent, to give compounds of the formula (VIII) which are then reacted with compounds of the formula (II), if appropriate in the presence of an acid binder and if appropriate in the presence of a diluent. The starting materials of the formula (VII) can be prepared, for example, by the process described by Bushey, Hoover, J. Org. Chem. 45, 4198 (1980).

Suitable acid binders for the reaction according to the process (C) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, polymeric bases, such as, for example, diisopropylaminopolystyrene, furthermore, alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for the process (C) according to the invention are all solvents which are inert to the halogenating agents. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, moreover nitriles, such as acetonitrile, and also strongly polar solvents, such as dimethyl sulphoxide and sulpholane.

The reaction temperature in the process (C) according to the invention can be varied within a relatively wide range. In general, the reaction is carried out at temperatures between −20° C. and 100° C., preferably between 0° C. and 80° C.

The process (C) according to the invention is generally carried out under atmospheric pressure.

When carrying out the process (C) according to the invention, the starting materials of the formula (VII) and the corresponding halogenating agent are generally each employed in approximately equivalent amounts. However, it is also possible to use a relatively large excess (up to 3 mol) of one or the other component. Work-up is carried out by customary methods. In general, precipitated salts are removed and the reaction mixture that remains is concentrated by removing the diluent under reduced pressure.

The process (D) is characterized in that compounds of the formula (I) in which Ar, V, X, $Y^1$, $Y^2$, $Y^3$, $Y^4$, $Y^5$, $Y^6$ and m are as defined above, K represents oxygen and Z represents hydrogen are in each case reacted with alkylating agents, acylating agents, sulphonylating agents or condensing agents of the formula (IX), if appropriate in the presence of a diluent and if appropriate in the presence of an acid binder. The alkylating agents, acylating agents, sulphonylating agents or condensing agents of the formula (IX) to be used are known chemicals for synthesis of organic chemistry.

Suitable diluents for the process (D) according to the invention are all solvents which are inert to the reagents mentioned above. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as, for example, dimethyl sulphoxide, dimethylformamide, N-methylpyrrolidone and sulpholane. The hydrolytic stability of the acylating agents and sulphonylating agents permitting, the reaction can also be carried out in the presence of water.

Suitable acid binders for the reaction according to the process (D) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide, furthermore alkali metal hydrides, such as sodium hydride, potassium hydride, or alkali metal alkoxides, such as potassium tert-butoxide.

The reaction temperatures in the process (D) according to the invention can be varied within a relatively wide range. In general, the reaction is carried out at temperatures between −70° C. and +150° C., preferably between −20° C. and 100° C. When carrying out the process (D) according to the invention, the starting materials of the formula (I) mentioned above and the abovementioned reagents of the formula (IX) are generally each employed in approximately equivalent amounts. However, it is also possible to use a relatively large excess (up to 5 mol) of the above-mentioned reagents. Work-up is carried out by customary methods.

Preferred catalysts for carrying out the process (E) according to the invention are palladium(0) complexes. Preference is given, for example, to tetrakis(triphenylphosphine)palladium.

Some of the arylboronic acids required for carrying out the process (E) are commercially available, such as, for example, 4-chloro-phenylboronic acid, or they can be prepared by known processes.

Suitable acid acceptors for carrying out the process (E) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate or ammonium carbonate, sodium bicarbonate or potassium bicarbonate, alkali metal fluorides, such as, for example, cesium fluoride, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicycloundecene (DBU), diazabicyclononene (DBN).

Suitable diluents for carrying out the process (E) according to the invention are water, organic solvents and any mixtures thereof. Examples which may be mentioned are: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl ether, diisopropyl ether, methyl tert-butyl ether, methyl tert-amyl ether, dioxane, tetrahydrofuran, 1,2-dimethoxyethane, 1,2-diethoxyethane, diethylene glycol dimethyl ether or anisole; alcohols, such as methanol, ethanol, n- or i-propanol, n-, iso-, sec- or tert-butanol, ethane-diol, propane-1,2-diol, ethoxyethanol, methoxyethanol, diethylene glycol monomethyl ether, diethylene glycol monoethyl ether; water.

The reaction temperature in the process (E) according to the invention can be varied within a relatively wide range. In general, the reaction is carried out a temperatures between 0° C. and +140° C., preferably between 50° C. and +100° C.

When carrying out the process (E) according to the invention, the boronic acid of the formula (X) in which $Ar^2$ is as defined above, and compounds of the formula (II), in which $Ar^1$, K, V, X, $Y^1$, $Y^2$, $Y^3$, $Y^4$, $Y^5$, $Y^6$, Z, m and Hal are as defined above, are employed in a molar ratio of from 1:1 to 3:1, preferably from 1:1 to 2:1. The catalyst is generally employed in amounts of from 0.005 to 0.5 mol, preferably from 0.01 to 0.1 mol per mole of the compound of the formula ($I^1$). The base is generally employed in excess.

The process (F) is characterized in that compounds of the formula (I) in which Ar, V, X, $Y^1$, $Y^2$, $Y^3$, $Y^4$, $Y^5$, $Y^6$, Z and m are as defined above and K represents oxygen are reacted with sulphurizing agents, if appropriate in the presence of a diluent.

The sulphurizing agents to be used are known chemicals for synthesis, such as, for example, phosphorus pentasulphide or 2,4-bis-(4-methoxyphenyl)-1,2,3,4-dithiaphosphetane-2,4-disulphide (Lawesson's Reagent).

Suitable diluents for the process (F) according to the invention are all solvents which are inert to the abovementioned reagents. Preference is given to using hydrocarbons, such as, for example, benzine, benzene, toluene, xylene and tetralin, furthermore halogenated hydrocarbons, such as methylene chloride, chloroform, chlorobenzene and o-dichlorobenzene, ethers, such as tetrahydrofuran, dioxane, diisopropyl ether or methyl tert-butyl ether.

The reaction temperatures in the process (F) according to the invention can be varied within a relatively wide range. In general, the reaction is carried out at temperatures between 0° C. and 250° C., preferably between 40° C. and 200° C.

When carrying out the process (F) according to the invention, the starting materials of the formula (I) and the abovementioned reagents are generally each employed in approximately equivalent amounts. However, it is also possible to use a relatively large excess of up to 5 mol of the abovementioned reagents. Work-up is carried out by customary methods.

The process (G) is characterized in that compounds of the formula (I) in which Ar, K, X, $Y^1$, $Y^2$, $Y^3$, $Y^4$, $Y^5$, $Y^6$ and m are as defined above and V represents a sulphur atom are reacted with an oxidizing agent, such as, for example, peracetic acid, perpropionic acid, perphthalic acid, m-chloroperbenzoic acid or hydrogen peroxide in the presence of molybdates or tungstates, in the presence of a diluent which is inert to the oxidizing agents.

Preferred diluents for the process (G) according to the invention are halogenated hydrocarbons, such as methylene chloride, chloroform, chlorobenzene, o-dichlorobenzene, furthermore carboxylic esters, such as ethyl acetate, or strongly polar solvents, such as dimethyl sulphoxide and sulpholane.

The reaction temperature in the process (G) according to the invention can be varied within a relatively wide range. In general, the reaction is carried out at temperatures between −30° C. and 100° C., preferably between −10° C. and 80° C.

When carrying out the process (G) according to the invention, the starting materials of the formula (I) and the oxidizing agent are generally employed in a molar ratio of 1:1 or 1:2. However, it is also possible to use a relatively large excess (up to 5 mol) of one or the other component. Work-up is carried out by customary methods.

The process (G) according to the invention is generally carried out under atmospheric pressure.

The active compounds according to the invention are particularly suitable for use as defoliants, desiccants, haulm-killers and, especially, as weed-killers. By weeds, in the broadest sense, are to be understood all plants which grow in locations where they are undesired. Whether the substances according to the invention act as total or selective herbicides depends essentially on the amount used.

The dosages of the active compounds according to the invention required for weed control are between 0.001 and 10 kg/ha, preferably between 0.005 and 5 kg/ha. The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: Allium, Ananas, Asparagus, Avena, Hordeum, Oryza, Panicum, Saccharum, Secale, Sorghum, Triticale, Triticum, Zea.

However, the use of the active compounds according to the invention is in no way restricted to these genera, but also extends in the same manner to other plants.

According to the invention, it is possible to treat all plants and parts of plants. By plants are to be understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders certificates. Parts of plants are to be understood as meaning all above-ground and below-ground parts and organs of plants, such as shoot, leaf, flower and root, examples which may be mentioned being leaves, needles, stems, trunks, flowers, shoot-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

The compounds are suitable, depending on the concentration, for the total control of weeds, for example on industrial terrain and rail tracks, and on paths and squares with or without tree plantings. Equally, the compounds can be employed for controllling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual crops.

The active compounds according to the invention are highly suitable for the selective control of monocotyledonous weeds in dicotyledonous crops by the pre- and post-emergence method. They can be used very successfully, for example, for the control of harmful grasses in cotton or sugar beet.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound and very fine capsules in polymeric substances.

These formulations are prepared in a known manner, for example by mixing the active compounds with extenders, that is liquid solvents and/or solid carriers, if appropriate with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene, or alkylnaphthalenes, chlorinated aromatics and chlorinated aliphatic hydrocarbons, such as chlorobenzene, chloroethylene or methylene chloride, aliphatic hydrocarbons, such as cyclohexane or paraffins, for example mineral oil fractions, mineral or vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%, and in addition preferably extenders and/or surfactants.

The active compound according to the invention can be present in its commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia. In preferred embodiments of the present invention, it is also possible to mix safeners with the compounds according to the invention, to increase crop plant compatibility.

Examples of particularly advantageous mixing components are the following:

Fungicides:

aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichiamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-∃-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-tri fluoromethoxy-4'-trifluoromethyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano[(1-methyl-2-propinyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholinehydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxymethanimidamide,
N-formyl-N-hydroxy-DL-alanine sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one, Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides:
abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-5-methyl, diafenthiuron, diazinon, dichlorvos, diflubenzuron, dimethoat, dimethylvinphos, diofenolan, disulfoton, docusat-sodium, dofenapyn,
eflusilanate, emamectin, empenthrin, endosulfan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses,
halofenozide, HCH, heptenophos, hexaflumuron, hexythiazox, hydroprene, imidacloprid, isazofos, isofenphos, isoxathion, ivermectin,
lambda-cyhalothrin, lufenuron,
malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos,
naled, nitenpyram, nithiazine, novaluron, nuclear polyhedrosis viruses,
omethoat, oxamyl, oxydemethon M,
Paecilomyces fumosoroseus, parathion A, parathion M, permethrin, phenthoat, phorat, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, sulfotep, suiprofos,
tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, *Verticillium lecanii*,
YI 5302,
zeta-cypermethrin, zolaprofos,
(1R-cis)-[5-(phenylmethyl)-3-furanyl]-methyl-3-[(dihydro-2-oxo-3(2H)-furanylidene)-methyl]-2,2-dimethylcyclopropanecarboxylate,
(3-phenoxyphenyl)-methyl-2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydro-oxazole,
2-(acetlyoxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazoldinylidene]-cyanamide,
dihydro-2-(nitromethylene)-2H-1,3-thiazine-3(4H)-carboxaldehyde,
ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N"-nitroguanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl [2-(dipropylamino)-2-oxoethyl]-ethylphosphoramidothioate.

Herbicides:
acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzobicyclon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlornitrofen, chlorsulfuron, chlortoluron, cinidon(-ethyl), cinmethylin, cinosulfuron, clefoxydim, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron(-methyl), ethofumesate, ethoxyfen, ethoxysulfuron, etobenzanid, enoxaprop(—P-ethyl), fentrazamide, flamprop(-isopropyl), flamprop(-isopropyl-L), flamprop(-methyl), flazasulfuron, florasulam, fluazifop(—P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate(-isopropylammonium), halosafen, haloxyfop-(-ethoxyethyl), haloxyfop(—P-methyl), hexazinone, imazamethabenz(-methyl), imazamethapyr, imazamox, imazapic, imazapyr, imazaquin, imazethapyr, imazosulfuron, iodosulfuron(-methyl, -sodium), ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quinmerac, quinoclamine, quizalofop(—P-ethyl), quizalofop(—P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

Furthermore, the active compound according to the invention, in its commercial formulations and in the use forms prepared from these formulations, can be present as a mixture with synergists. Synergists are compounds which increase the activity of the active compounds without it being necessary for the added synergist to be active itself.

The active compound content of the use forms prepared from the commercial formulations can vary within wide ranges. The concentration of active compound in the use forms can be from 0.0000001 to 95% by weight of active compound, preferably between 0.0001 and 1% by weight.

Application is carried out in a customary manner adapted to the use forms.

The active compounds are furthermore suitable for controlling animal pests, preferably arthropods and nematodes, in particular insects and arachnids, which are encountered in agriculture, in forestry, in the protection of stored products and of materials, and in the hygiene sector. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Blattaria or Orthoptera, for example, *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregana.*

From the order of the *Dermaptera*, for example, *Forficula auricularia.*

From the order of the *Isoptera*, for example, *Reticulitermes* spp.

From the order of the Anoplura, for example, *Phylloxera vastatrix, Pemphigus* spp., *Pediculus humanus corporis, Haematopinus* spp. and *Linognathus* spp.

From the order of the Mallophaga, for example, *Trichodectes* spp. and *Damalinea* spp.

From the order of the Thysanoptera, for example, *Frankliniella occidentalis, Hercinothrips femoralis, Thrips palmi* and *Thrips tabaci*.

From the ordeer of the Heteroptera, for example, *Eurygaster* spp., *Dysdercus intermedius, Piesma quadrata, Cimex lectularius, Rhodnius prolixus* and *Triatoma* spp.

From the order of the *Homoptera*, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Phylloxera vasturix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantil, Aspidiotus hederae, Pseudococcus* spp. and *Psylla* spp.

From the order of the *Lepidoptera*, for example, *Pectinophora gossypiella, Bupalus piniarius, Cheimatobia brumata, Lithocolletis blancardella, Hyponomeuta padella, Plutella maculipennis, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Spodoptera exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Aulema oryzae*.

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon soistitialis, Costelytra zealandica* and *Lissorhoptus oryzophilus*.

From the order of the *Hymenoptera*, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Liriomyza* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemnia* spp. and *Liviomyza* spp.

From the order of the *Siphonaptera*, for example, *Xenopsylla cheopis* and *Ceratophyllus* spp.

From the order of the Arachnida, for example, *Scorpio maurus* and *Latrodectus mactans*.

From the order of the Acarina, for example, *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipulpus* spp.

The phytoparasitic nematodes include, for example, *Pratylenchus* spp. *Radopholus similis, Ditylenchus dipsaci, Tylenchulus semi penetrans, Heteroderma* spp., *Globodera* spp., *Meloidogyne* spp., *Aphelenchoides* spp., *Longidorus* spp., *Xiphinema* spp., *Trichodorus* spp. and *Bursaphelenchus* spp.

The active compounds according to the invention have high insecticidal and acaricidal activity after foliar and soil application.

At certain concentrations or application rates, the compounds according to the invention also have fungicidal action. Furthermore, they can also be used as microbicides or antimycotics.

When used against hygiene pests and pests of stored products, the active compound has excellent residual activity on wood and clay, and by good stability to alkali on limed substrates.

The active compounds according to the invention act not only against plant, hygiene and stored-product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana*, Blattela germanica and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp.,

*Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100- to 10,000-fold dilution, or they can be used as a chemical bath.

It has furthermore been found that the compounds of the formula (I) according to the invention also have a strong insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec. and *Dinoderus minutus.*

Hymenopterons, such as

*Sirex juvencus, Urocerus gigas, Urocerus gigas taignus* and *Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus.*

Bristletails, such as

*Lepisma saccarina.*

Industrial materials in the present connection are to be understood as meaning nonliving materials, such as, preferably, plastics, adhesives, sizes, papers and cardboards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example: building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the protection of wood and timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be protected.

Solvents and/or diluents which are used are an organochemical solvent or solvent mixture and/or an oily or oil-like organochemical solvent or solvent mixture of low volatility and/or a polar organochemical solvent or solvent mixture and/or water, and if appropriate an emulsifier and/or wetting agent.

Organochemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organochemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organochemical solvent or solvent mixture is replaced by an aliphatic polar organochemical solvent or solvent mixture. Aliphatic organochemical solvents containing hydroxyl and/or ester and/or ether groups, such as, for example, glycol ethers, esters or the like, are preferably used.

Organochemical binders which are used in the context of the present invention are the synthetic resins and/or binding drying oils which are known per se, are water-dilutable and/or are soluble or dispersible or emulsifiable in the organochemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organochemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organochemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing components are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The active compounds according to the invention can be used particularly effectively for controlling plant-damaging insects, such as, for example, against the larvae of the mustard beetle (Phaedon cochleariae), against the larvae of the green rice leafhopper (*Nephotettix cincticeps*) and against the larvae of the green peach aphid (*Myzus persicae*).

In addition to the acaricidal, herbicidal and insecticidal properties described, a fungicidal activity of the active compounds according to the invention is noticeable. In both 'in vitro' and 'in vivo' studies, a broad fungicidal effect can be observed.

Moreover, it was noticed that the active compounds are, in particular, also suitable for controlling mildew, leaf blotch and Fusaria on the infected plants.

The preparation and the use of the active compounds according to the invention is shown in the examples below.

PREPARATION EXAMPLES

Example 1

Comp. No. I-1-a-1

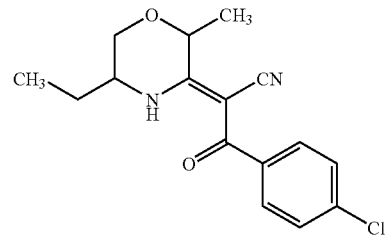

(Process A)

A mixture of 1.75 g of 5-ethyl-2-methyl-5,6-dihydro-2H-1,4-oxazin-3-yl methyl sulphide and 1.80 g of 4-chlorobenzoylacetonitrile in 10 ml of toluene is heated to 110° C. The reaction is monitored by thin-layer chromatography. Once the starting materials have been converted virtually completely, the mixture is cooled and the compounds contained therein are separated column-chromatographically over a silica gel phase using hexane/ethyl acetate (2:1) as mobile phase.

One of the main fractions gave, after evaporation of the solvent, 0.25 g (8.3% of theory) of 3-(4-chlorophenyl)-2-(5-ethyl-2-methyl-1,4-oxazinon-3-ylidene)-3-oxopropionitrile of melting point 136° C.

$^1$H-NMR (400 MHz, d$_6$-DMSO): δ=0.97 (t, 3H, CH$_2$—CH$_3$); 1.62 (d, 3H, CHCH$_3$); 4.76 (m, 1H, O—CH—CH$_3$); 7.56, 7.7 (2AA'BB', 4H, ArH); 12.4 (s, 1H, NH) ppm.

Example 2

Comp. No. I-1-a-2

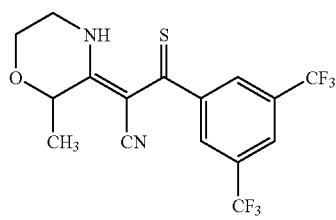
(Process F)

A mixture of 0.6 g of 3-[3,5-bis(trifluoromethyl)phenyl]-2-(2-methyl-1,4-oxazinan-3-ylidene)-3-oxopropionitrile and 0.5 g of Lawesson's Reagent is heated under reflux for 2 hours. The reaction products in the mixture are then separated column-chromatographically over a silica gel phase using hexane/ethyl acetate (2:1) as mobile phase.

One of the main fractions gives, after evaporation of the solvent, 0.5 g (85% of theory) of 3-[3,5-bis(trifluoromethyl)phenyl]-2-(2-methyl-1,4-oxazinan-3-ylidene)-3-thioxopropionitrile of melting point 195° C.

Example 3

Comp. No. III-1

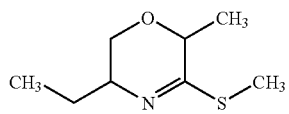

At 0° C., 8.5 g of KOH are added to 10.6 g of 5-ethyl-2-methyl-3-morpholinethione in 150 ml of acetone. The mixture is warmed to room temperature (20° C.) and 5 ml of methyl iodide are added. The mixture is allowed to react for four hours, and the solvent is then distilled off under reduced pressure. The solid residue that remains is separated column-chromatographically over a silica gel phase using hexane/ethyl acetate (10:1).

The main fraction gave, after evaporation of the solvent, 7.6 g (65.5% of theory) of 5-ethyl-2-methyl-5,6-dihydro-2H-1,4-oxazin-3-yl methyl sulphide as a yellow oil.

Example 4

Comp. No. V-I

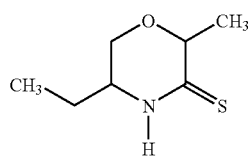

At room temperature (20° C.), a mixture of 20 g of 5-ethyl-2-methyl-3-morpholinone and 100 ml of toluene is admixed with 33 g of Lawesson's Reagent. The reaction mixture is then heated at reflux for 24 hours. Work-up is carried out analogously to Example 2.

This gives 11.2 g (50% of theory) of 5-ethyl-2-methyl-3-morpholinethione as an oil.

Example 5

Comp. No. I-2-A-a-i

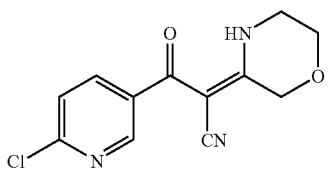
(Process A)

A mixture of 1.0 g of 6-chloro-3-pyridinylacetonitrile, 1.27 g of 5,6-dihydro-2H-1,4-oxazin-3-yl methyl sulphide (preparation analogous to Example 3) and 10 ml of toluene is heated to 80° C. and stirred at this temperature for 5 hours. The solvent is then distilled off under reduced pressure, giving a solid residue which is recrystallized from a mixture of methyl tert-butyl ether (MTBE) and cyclohexane The resulting solid of melting point 179° C. is dried.

This gives 1.24 g (85.2% of theory) of 3-(6-chloro-3-pyridinyl)-2-(1,4-oxazinan-3-ylidene)-3-oxopropionitrile.

Example 6

Comp. No. I-1-a-15

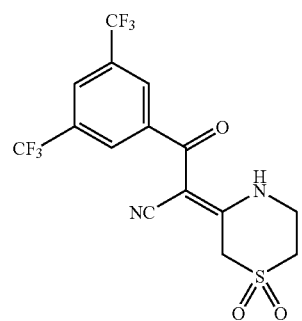
(Process G)

0.5 g of 3-[3,5-bis(trifluoromethyl)phenyl]-2-(1,4-thiazinan-3-ylidene)-3-oxo-propionitrile (Comp. No. I-1-a-10) is introduced into 20 ml of chloroform and, at 20° C., admixed with 0.35 g of 3-chloroperbenzoic acid. The progress of the reaction was monitored by thin-layer chromatography. After all of the starting material has been converted, the reaction product is extracted with an $NaHCO_3$ solution and separated column-chromatographically over a silica gel phase using dichloromethane/ethyl acetate (10:1) as mobile phase. The main fraction gives, after evaporation of the solvent, 0.50 g of 3-[3,5-bis(trifluoromethyl)phenyl]-2-(1,1-dioxo-1$\lambda^{6,4}$-thiazinan-3-ylidene)-3-oxo-propionitrile having a melting range of from 224 to 226° C.

Example 7

Comp. No. I-1-a-37

(Process E)

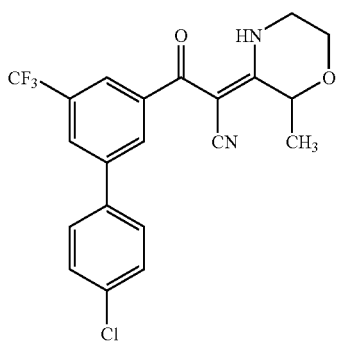

Under argon, 1.2 g of 3-(3-bromo-5-trifluoromethylphenyl)-2-(2-methyl-1,4-oxazinon-3-ylidene)-3-oxopropionitrile (Comp. No. I-1-a-24) are added to 30 ml of dimethoxyethane and admixed with 0.5 g of 4-chlorophenylboronic acid, 200 mg of tetrakis-triphenylphosphine and 30 ml of a 2 molar $K_2CO_3$ solution. The reaction mixture is heated at 80° C. overnight.

The compounds contained in the reaction mixture are then separated column-chromatographically over a silica gel phase using hexane/ethyl acetate (2:1) as mobile phase.

One of the main fractions gave, after evaporation of the solvent, 0.65 g (52% of theory) of 3-[3-(4-chlorophenyl)-5-trifluoromethylphenyl]-2-(2-methyl-1,4-oxazinon-3-ylidene)-3-oxopropionitrile of melting point 119° C.

Analogously to Example 1 and Example 2, and in accordance with the general statements on the preparation of compounds of the formula (1-1-a), the following compounds are obtained:

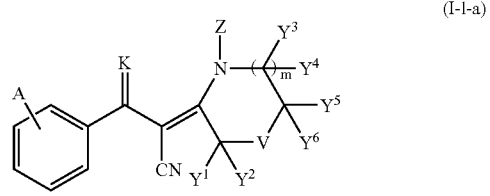

(I-1-a)

| Comp. No. | K | A | m | $Y^1$ | $Y^2$ | $Y^3$ | $Y^4$ | $Y^5$ | $Y^6$ | V | Z | m.p. ° C. |
|---|---|---|---|---|---|---|---|---|---|---|---|---|
| I-1-a-3 | O | 4-Cl | 1 | H | H | $C_2H_5$ | H | H | H | O | H | Oil |
| I-1-a-4 | O | 4-(4-Cl-$C_6H_4$), 2-F | 1 | H | H | H | H | H | H | O | H | 198 |
| I-1-a-5 | O | 4-Cl | 1 | H | H | H | H | H | H | O | H | 192 |
| I-1-a-6 | O | 2-$CF_3$ | 1 | H | H | H | H | H | H | O | H | 158 |
| I-1-a-7 | O | 3,5-$(CF_3)_2$ | 1 | H | H | H | H | H | H | O | H | 164 |
| I-1-a-8 | O | 2,4-$F_2$ | 1 | H | H | H | H | H | H | O | H | 179 |
| I-1-a-9 | O | 4-CN | 1 | H | H | H | H | H | H | O | H | 224 |
| I-1-a-10 | O | 3,5-$(CF_3)_2$ | 1 | H | H | H | H | H | H | S | H | 182 |
| I-1-a-11 | O | 3,5-$(CF_3)_2$ | 1 | H | H | $CH_3$ | $CH_3$ | H | H | O | H | Oil |
| I-1-a-12 | O | 3,5-$(CF_3)_2$ | 1 | H | H | $C_2H_5$ | H | H | H | O | H | Oil |
| I-1-a-13 | O | 3,5-$(CF_3)_2$ | 1 | $CH_3$ | H | $C_2H_5$ | H | H | H | O | H | 72 |
| I-1-a-14 | O | 3,5-$(CF_3)_2$ | 1 | $CH_3$ | H | H | H | H | H | O | H | 142 |
| I-1-a-15 | O | 3,5-$(CF_3)_2$ | 1 | $CH_3$ | H | H | H | H | H | $SO_2$ | H | 224–226 |
| I-1-a-16 | O | 4-Cl | 1 | H | H | $CH_3$ | $CH_3$ | H | H | O | H | 102 |
| I-1-a-17 | O | 4-Cl | 1 | H | H | H | H | $CH_3$ | H | O | H | 235 |
| I-1-a-18 | O | 3,5-$(CF_3)_2$ | 1 | H | H | H | H | $CH_3$ | H | O | H | 157 |
| I-1-a-19 | O | 3,5-$(CF_3)_2$ | 1 | $CH_3$ | H | H | H | $CH_3$ | H | O | H | 142 |
| I-1-a-20 | O | 4-Cl | 1 | $CH_3$ | H | H | H | $CH_3$ | H | O | H | 179 |
| I-1-a-21 | O | 4-Me | 1 | $CH_3$ | H | H | H | H | H | O | H | Oil |
| I-1-a-22 | O | 4-Cl | 1 | H | H | H | H | H | H | S | H | 182–184 |
| I-1-a-23 | O | 3-(3-Cl—$C_6H_4$—O), 5-$NO_2$ | 1 | $CH_3$ | H | H | H | H | H | O | H | |
| I-1-a-24 | O | 3-Br, 5-$CF_3$ | 1 | $CH_3$ | H | H | H | H | H | O | H | 126 |
| I-1-a-25 | O | 3,5-$(CH_3)_2$ | 1 | $CH_3$ | H | H | H | H | H | O | H | Oil |
| I-1-a-26 | O | 3,5-$Br_2$ | 1 | $CH_3$ | H | H | H | H | H | O | H | 211 |
| I-1-a-27 | O | 3,5-$Br_2$ | 1 | H | H | H | H | H | H | O | H | 226 |
| I-1-a-28 | O | 4-Br, 2-F | 1 | H | H | H | H | H | H | O | H | 192 |
| I-1-a-29 | O | 4-Cl | 1 | $CH_3$ | H | H | H | H | H | O | H | 194 |
| I-1-a-30 | S | 4-Cl | 1 | H | H | H | H | H | H | O | H | 194 |
| I-1-a-31 | S | 3,5$(CF_3)_2$ | 1 | H | H | H | H | H | H | O | H | 217 |
| I-1-a-32 | O | 4-Cl | 1 | $CH_3$ | $CH_3$ | H | H | H | H | S | H | 191 |
| I-1-a-33 | O | 3,5-$(CF_3)_2$ | 1 | $CH_3$ | $CH_3$ | H | H | H | H | S | H | 142 |
| I-1-a-34 | O | 4-Cl | 1 | —$(CH_2)_3$— | | H | H | H | H | S | H | 171 |
| I-1-a-35 | O | 3,5-$(CF_3)_2$ | 1 | —$(CH_2)_3$— | | H | H | H | H | S | H | 156 |
| I-1-a-36 | O | 3-$CF_3$-5-(4-$CF_3$—$C_6H_4$) | 1 | $CH_3$ | H | H | H | H | H | O | H | 146 |
| I-1-a-37 | O | 3-$CF_3$-5-(4-Cl—$C_6H_4$) | 1 | $CH_3$ | H | H | H | H | H | O | H | 119 |

Analogously to Example 5 and in accordance with the general statements on the preparation of the compounds of the formula (I-1-a), the following compounds of the formula (I-2-a) are obtained.

(1-2-A-a)

(1-2-B-a)

| Comp. No. | K | A | m | $Y^1$ | $Y^2$ | $Y^3$ | $Y^4$ | $Y^5$ | $Y^6$ | V | m.p. °C. |
|---|---|---|---|---|---|---|---|---|---|---|---|
| I-2-A-a-2 | O | 4,6-$Cl_2$ | 1 | H | H | H | H | H | H | O | 140 |
| I-2-A-a-2 | O | 2-Cl | 1 | H | H | H | H | H | H | O | 164 |
| I-2-A-a-4 | O | 6-Cl | 1 | H | H | $CH_3$ | $CH_3$ | H | H | O | |
| I-2-A-a-5 | O | 2-Cl | 1 | $CH_3$ | H | H | H | H | H | O | 140 |
| I-2-A-a-6 | O | 4,6-Cl | 1 | $CH_3$ | H | H | H | H | H | O | 108 |
| I-2-A-a-7 | O | 6-Cl | 1 | $CH_3$ | H | H | H | H | H | O | 189 |
| I-2-B-a-1 | O | 2,6-$Cl_2$ | 1 | $CH_3$ | H | H | H | H | H | O | 174 |

Example

*Phaedon larvae* test
Solvent: 31 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the following compounds of the Preparation Examples show good activity: I-1-a-10.

Example

*Spodoptera frugiperda* test
Solvent: 31 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with emulsifier-containing water to the desired concentration.

A stated amount of the preparation of active compound of the desired concentration is pipetted onto a standardized amount of synthetic feed. In 6 repetitions, in each case one larva (L3) of the army worm (*Spodoptera frugiperda*) is placed on the feed.

After the desired period of time, the kill in % is determined. 100% means that all animals have been killed; 0% means that none of the animals have been killed.

In this test, for example, the following compounds of the Preparation Examples show good activity: I-1-a-14.

Example

*Heliothis virescens* test
Solvent: 30 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Soya bean shoots (*Glycine max*) are treated by being dipped into the preparation of active compound of the desired concentration and populated with *Heliothis virescens* caterpillars while the leaves are still moist.

After the desired period of time, the kill in % is determined. 100% means that all caterpillars have been killed; 0% means that none of the caterpillars have been killed.

In this test, for example, the following compounds of the Preparation Examples show good activity: I-1-a-14.

Example

*Tetranychus* test (OP resistent/dip treatment)
Solvent: 30 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the common spider mite (*Tetranychus urticae*) are dipped into a preparation of active compound of the desired concentration.

After the desired period of time, the kill in % is determined. 100% means that all spider mites have been killed; 0% means that none of the spider mites have been killed.

In this test, for example, the following compounds of the Preparation Examples show good activity: I-1-a-10, I-1-a-7.

Example

Post-emergence test
Solvent: 5 parts by weight of acetone
Emulsifier: 1 part by weight of alkylaryl polyglycol ether
To produce a suitable preparation of active compound, 1 part by weight of active compound is mixed with the stated amount of solvent, the stated amount of emulsifier is added and the concentrate is diluted with water to the desired concentration.

Test plants of a height of 5 to 15 cm are sprayed with the preparation of active compound such that the particular amounts of active compound desired are applied per unit area. After 3 weeks, the degree of damage to the plants is rated in % damage in comparison to the development of the untreated control.

The figures denote:
  0%=no effect (like untreated control)
  100%=total destruction
In this test, for example, the compounds of Preparation Examples I-1-a-7, I-1-a-8, I-1-a-9 exhibit strong activity against weeds, and some of them are tolerated well by crop plants, such as, for example, wheat.

Example

Pre-emergence test
Solvent: 5 parts by weight of acetone
Emulsifier: 1 part by weight of alkylaryl polyglycol ether
To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of active compound. The amount of water per unit area is advantageously kept constant. The concentration of active compound in the preparation is immaterial, only the active compound application rate per unit area matters. After three weeks, the degree of damage to the plants is rated in % damage in comparison to the development of the untreated control.

The figures denote:
  0%=no effect (like untreated control)
  100%=total destruction
In this test, for example, the compounds of Preparation Examples I-1-a-3, I-1-a-7, I-1-a-8, I-1-a-9 exhibit strong activity against weeds, and some of them are tolerated well by crop plants, such as, for example, wheat and soya.

What is claimed is:
1. A compound of the Formula (I)

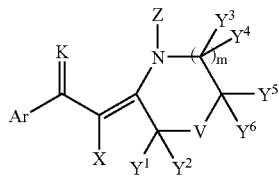

wherein
  K represents oxygen or sulphur,
  Ar represents in each case substituted phenyl or naphthyl or represents in each case optionally substituted mono- or bicyclic hetaryl having 5 to 10 ring atoms,
  V represents oxygen,
  X represents CN,

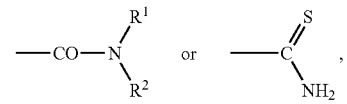

$Y^1$ and $Y^3$ independently of one another represent hydrogen, halogen or in each case optionally substituted alkyl, alkoxy, alkoxyalkyl, phenyl, phenylalkyl, hetaryl, hetarylalkyl or represent the groups

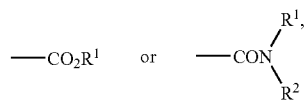

and
  $Y^2$, $Y^4$, $Y^6$ independently of one another represent hydrogen, halogen or optionally substituted alkyl,
  $Y^5$ represents hydrogen or in each case optionally substituted alkyl or phenyl, or
  $Y^4$ and $Y^5$ together with the carbon atoms to which they are attached represent an optionally substituted saturated or unsaturated cycle which is optionally interrupted by heteroatoms, or
  $Y^1$ and $Y^2$ together with the carbon atom to which they are attached represent an optionally substituted cycle which is optionally interrupted by heteroatoms,
  Z represents hydrogen, represents in each case optionally substituted alkyl, alkenyl, alkinyl, cycloalkyl, cycloalkyl-alkyl, alkoxyalkyl, phenoxyalkyl, phenylalkyl-oxyalkyl, phenylthioalkyl, phenylalkyl-thioalkyl, phenyl, phenylalkyl, hetaryl, hetaryl-alkyl or represents the groups

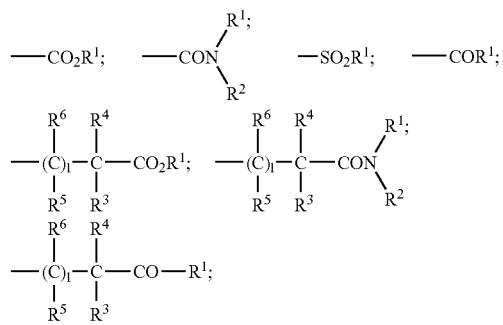

or cyano,
  l represents 0 to 3,
  m represents 0 to 2,
  $R^1$ represents hydrogen, represents in each case optionally substituted, saturated or unsaturated alkyl or cycloalkyl, each of which is optionally interrupted by heteroatoms, represents in each case optionally substituted phenyl or hetaryl, represents in each case optionally substituted phenylalkyl or hetarylalkyl,
  $R^2$ represents hydrogen, represents in each case optionally substituted, saturated or unsaturated alkyl or alkoxy, represents in each case optionally substituted phenyl, phenylalkyl or phenylalkyloxy, $R^1$, $R^2$ furthermore together with the nitrogen atom to which they are attached may represent an optionally substituted cycle which is optionally interrupted by heteroatoms, or $R^3$ represents hydrogen, represents in each case optionally substituted alkyl or alkoxy, represents in each case optionally substituted phenyl or phenylalkyl, $R^4$ represents hydrogen or represents optionally substituted alkyl, and $R^5$, $R^6$ independently of one another represent hydrogen or represent optionally substituted alkyl.

2. A compound according to claim 1, wherein

Ar represents $Ar^1$, where $Ar^1$ represents substituted phenyl or naphthyl or represents optionally substituted mono- or bicyclic hetaryl having five to ten ring atoms, each of which substituted radical is optionally mono- to pentasubstituted by halogen, $C_1$–$C_8$-alkyl, $C_2$–$C_8$-alkenyl, $C_2$–$C_8$-alkinyl, $C_1$–$C_8$-alkoxy, $C_2$–$C_8$-alkenyloxy, $C_3$–$C_8$-alkinyloxy, $C_1$–$C_8$-alkylthio, $C_1$–$C_6$-alkylsulphinyl, $C_1$–$C_6$-alkylsulphonyl, $C_1$–$C_6$-halogenoalkyl, $C_1$–$C_6$-halogeno-alkoxy, $C_2$–$C_8$-halogenoalkenyloxy, $C_1$–$C_2$-alkylidenediyl-dioxy, $C_1$–$C_2$-halogenoalkylidenediyl-dioxy, halogeno-$C_1$–$C_4$-alkylthio, halogeno-$C_1$–$C_4$-alkylsulphinyl, halogeno-$C_1$–$C_4$-alkylsulphonyl, hydroxyl, mercapto, nitro, cyano, amino or by the groups a)   —L—CO—$R^7$, b)   —N(—$R^8$)—C(=L)H, c)   —N(—$R^8$)—C(=L)—$R^7$, d)   —N(—$R^8$)—SO$_2R^7$, e)   —L—CH($R^5$)—CO—$R^7$, f)   —L—CH($R^5$)—CO$_2$H, g)   —C(=L)—$R^7$ or represents $Ar^2$, where $Ar^2$ represents $Ar^1$ which is additionally substituted by phenyl, naphthyl, five or six-membered hetaryl, phenyl-$C_1$–$C_4$-alkyl, phenyl-$C_1$–$C_4$-alkoxy, phenyl-$C_1$–$C_4$-alkyl-S(O)$_n$—, five- or six-membered hetaryl-$C_1$–$C_4$-alkoxy, five- or six-membered hetaryl-$C_1$–$C_4$-alkyl-S(O)$_p$—, phenoxy, phenyl-S(O)$_p$—, five- or six-membered hetaryloxy or hetaryl-S(O)$_p$—, where these substituents for their part are in each case optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, K represents oxygen or sulphur, L represents oxygen or sulphur, V represents oxygen, X represents CN, —CO—N($R^1$)($R^2$)   or   —C(=S)—NH$_2$, $Y^1$ and $Y^3$ independently of one another represent hydrogen, halogen, $C_1$–$C_6$-alkyl, $C_1$–$C_4$-halogenoalkyl, $C_1$–$C_6$-alkoxy, $C_1$–$C_6$-alkoxy-$C_1$–$C_2$-alkyl, represent phenyl, phenyl-$C_1$–$C_4$-alkyl, five- or six-membered hetaryl or five- or six-membered hetaryl-$C_1$–$C_4$-alkyl, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro or represent the groups —CO$_2R^1$   or   —CO—N($R^1$)($R^2$), $Y^2$, $Y^4$, $Y^6$ independently of one another represent hydrogen, halogen or represent fluorine- and/or chlorine-substituted $C_1$–$C_6$-alkyl, $Y^5$ represents hydrogen, represents optionally fluorine-substituted $C_1$–$C_6$-alkyl or represents phenyl which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, or $Y^4$ and $Y^5$ together with the carbon atoms to which they are attached represent a 5- to 8-membered saturated or unsaturated cycle which may be interrupted by 1 to 3 heteroatoms from the group consisting of N, O, S and which may optionally be mono- to trisubstituted by halogen, $C_1$–$C_4$-alkyl, $C_1$–$C_4$-alkoxy, $C_1$–$C_4$-halogenoalkyl, $C_1$–$C_4$-halogenoalkoxy, cyano or nitro, or $Y^1$ and $Y^2$ together with the carbon atom to which they are attached represent a $C_3$–$C_6$-cycloalkyl ring, Z represents hydrogen, represents in each case optionally fluorine- and/or chlorine-substituted $C_1$–$C_8$-alkyl, cyano-$C_1$–$C_6$-alkyl, $C_3$–$C_8$-alkenyl, $C_3$–$C_8$-alkinyl, $C_3$–$C_8$-cycloalkyl, $C_3$–$C_8$-cycloalkyl-$C_1$–$C_2$-alkyl, $C_1$–$C_4$-alkoxy-$C_1$–$C_4$-alkyl, $C_1$–$C_4$-halogenoalkoxy-$C_1$–$C_4$-alkyl, represents phenoxy-$C_1$–$C_4$-alkyl, phenyl-$C_1$–$C_4$-alkyloxy-$C_1$–$C_4$-alkyl, phenylthio-$C_1$–$C_4$-alkyl, phenyl-$C_1$–$C_4$-alkylthio-$C_1$–$C_4$-alkyl, phenyl, phenyl-$C_1$–$C_4$-alkyl, five- or six-membered hetaryl, five- or six-membered hetaryl-$C_1$–$C_4$-alkyl, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano or represents the groups

—CO$_2R^1$;   —CON($R^1$)($R^2$);   —SO$_2R^1$;   —COR$^1$;

—(C)$_l$(—$R^6$)(—$R^5$)—C(—$R^4$)(—$R^3$)—CO$_2R^1$;   —(C)$_l$(—$R^6$)(—$R^5$)—C(—$R^4$)(—$R^3$)—CON($R^1$)($R^2$)

-continued

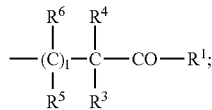

or cyano, p represents 0 to 2, l represents 0 to 2, $R^1$ represents hydrogen (but not in the radicals —$CO_2R^1$ and —$SO_2R^1$), represents in each case optionally fluorine- and/or chlorine-substituted $C_1$–$C_{10}$-alkyl, $C_2$–$C_{10}$-alkenyl, $C_3$–$C_6$-alkinyl, represents in each case optionally fluorine-, chlorine-, $C_1$–$C_4$-alkyl-, $C_1$–$C_4$-alkoxy-substituted $C_3$–$C_8$-cycloalkyl or $C_5$–$C_8$-cycloalkenyl, in which optionally one methylene group may be interrupted by oxygen or sulphur, or represents phenyl, pyridyl, thienyl, pyrimidyl, thiazolyl, phenyl-$C_1$–$C_4$-alkyl, pyridyl-$C_1$–$C_2$-alkyl, thiazolyl-$C_1$–$C_2$-alkyl, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^2$ represents hydrogen, represents in each case optionally fluorine- and/or chlorine-substituted $C_1$–$C_6$-alkyl, $C_3$–$C_6$-alkenyl, $C_3$–$C_6$-alkinyl, $C_1$–$C_6$-alkoxy, $C_3$–$C_6$-alkenyloxy or represents phenyl, phenyl-$C_1$–$C_4$-alkyl or phenyl-$C_1$–$C_4$-alkoxy, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, or $R^1$, $R^2$ furthermore together with the nitrogen atom to which they are attached may represent a five- to eight-membered cycle in which optionally one methylene group may be replaced by oxygen or sulphur and which may in each case optionally be substituted by $C_1$–$C_4$-alkyl, $R^3$ represents hydrogen, optionally halogen-substituted $C_1$–$C_6$-alkyl or represents phenyl or phenyl-$C_1$–$C_2$-alkyl, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^4$ represents hydrogen or $C_1$–$C_6$-alkyl, $R^5$, $R^6$ independently of one another represent hydrogen or optionally fluorine- and/or chlorine-substituted $C_1$–$C_4$-alkyl, $R^7$ represents in each case optionally fluorine- and/or chlorine-substituted $C_1$–$C_{10}$-alkyl, $C_2$–$C_{10}$-alkenyl, $C_3$–$C_{10}$-alkinyl, $C_1$–$C_{10}$-alkoxy, $C_1$–$C_4$-alkoxy-$C_1$–$C_4$-alkyl, $C_1$–$C_4$-alkylthio-$C_1$–$C_4$-alkyl, in each case optionally fluorine-, chlorine-, $C_1$–$C_4$-alkyl- and/or $C_1$–$C_4$-alkoxy-substituted $C_3$–$C_8$-cycloalkyl or $C_3$–$C_8$-cycloalkoxy, in which optionally one methylene group may be replaced by oxygen or sulphur, represents phenyl, phenoxy, benzyloxy, five- or six-membered hetaryl or phenyl-$C_1$–$C_4$-alkyl, each of which may optionally be mono- to tetrasubstituted by halogen, $C_1$–$C_6$-alkyl, $C_1$–$C_6$-alkoxy, $C_1$–$C_4$-halogeno-alkyl, $C_1$–$C_4$-halogenoalkoxy, cyano or nitro or, in the case of the radicals a) and c) mentioned under Ar, also represents a group or, for the radical g), also represents hydroxyl, $R^8$ represents hydrogen or $C_1$–$C_4$-alkyl, $R^9$ represents hydrogen, in each case optionally fluorine- and/or chlorine-substituted $C_1$–$C_{10}$-alkyl, $C_3$–$C_8$-alkenyl, $C_3$–$C_8$-alkinyl, $C_1$–$C_{10}$-alkoxy, $C_3$–$C_8$-alkenyloxy, optionally fluorine-, chlorine-, $C_1$–$C_4$-alkyl- or $C_1$–$C_4$-alkoxy-substituted $C_3$–$C_8$-cycloalkyl, in which optionally one methylene group may be replaced by oxygen or sulphur, represents phenyl, phenyl-$C_1$–$C_4$-alkyl or phenyl-$C_1$–$C_2$-alkoxy, each of which may optionally be mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^{10}$ represents hydrogen, $C_1$–$C_6$-alkyl or $C_3$–$C_6$-alkenyl, or $R^9$, $R^{10}$ furthermore together with the nitrogen atom to which they are attached may represent an optionally $C_1$–$C_4$-alkyl-substituted five- to eight-membered cycle in which optionally one methylene group may be replaced by oxygen or sulphur, and m represents 0 to 2.

3. A compound according to claim 1, wherein

K represents oxygen or sulphur,

Ar represents $Ar^1$, where $Ar^1$ represents substituted phenyl, naphthyl, quinolinyl, thienyl, pyrimidyl, furanyl, thiazolyl, benzothiazolyl, oxazolyl, pyrazolyl or pyridyl, each of which is optionally mono- to trisubstituted by fluorine, chlorine, bromine, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_3$–$C_6$-alkinyloxy, $C_1$–$C_6$-alkylthio, $C_1$–$C_4$-alkylsulphinyl, $C_1$–$C_4$-alkylsulphonyl, $C_1$–$C_4$-halogenoalkyl, $C_1$–$C_4$-halogeno-alkoxy, $C_2$–$C_4$-halogenoalkenyloxy, $C_1$–$C_2$-alkylidenediyl-dioxy, $C_1$–$C_2$-halogenoalkylidenediyl-dioxy, halogen-$C_1$–$C_2$-alkylthio, halogen-$C_1$–$C_2$-alkylsulphinyl, halogen-$C_1$–$C_2$-alkylsulphonyl, hydroxyl, mercapto, nitro, cyano, amino or by one of the following groups a) —L—$COR^7$, b) 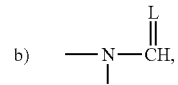

c) 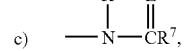

d) 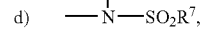

e) 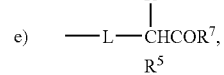

f) 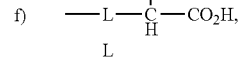

g) 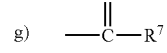

or represents Ar², where Ar² represents Ar¹ which is additionally substituted by phenyl, pyridyl, pyrimidyl, thienyl, furanyl, thiazolyl, tetrazolyl, triazolyl, benzyl, phenyl-$C_1$–$C_2$-alkoxy, phenyl-$C_1$–$C_2$-alkyl-$S(O)_p$—, thienyl-$C_1$–$C_2$alkoxy, thiazolyl-$C_1$–$C_2$-alkoxy, pyrimidyl-$C_1$–$C_2$-alkoxy, thiazolyl-$C_1$–$C_2$alkyl-$S(O)_p$—, pyridyl-$C_1$–$C_2$-alkyl-$S(O)_p$, phenoxy, phenyl-$S(O)_p$—, pyridyloxy, pyrimidyloxy, thiazolyloxy, pyridyl-$S(O)_p$—, pyrimidyl-$S(O)_p$— or thiazolyl-$S(O)_p$—, where these substituents for their part are optionally mono- to trisubstituted by fluorine, chlorine, bromine, C—$C_4$-alkyl, $C_2$–$C_4$-alkenyl, $C_1$–$C_4$-alkoxy, $C_1$–$C_2$-halogenoalkyl, $C_1$–$C_2$-halogenoalkoxy, nitro or cyano, L represents oxygen or sulphur,
V represents oxygen,
X represents CN,

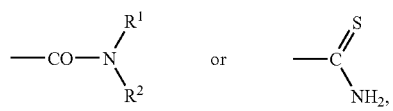

$Y^1$ and $Y^3$ independently of one another represent hydrogen, represent fluorine, $C_1$–$C_4$-alkyl, $C_1$–$C_2$-halogenoalkyl, $C_1$–$C_4$-alkoxy, $C_1$–$C_4$-alkoxy-$C_1$–$C_2$-alkyl, represents phenyl, thienyl, pyridyl, thiazolyl, pyrimidyl, phenyl-$C_1$–$C_2$-alkyl, thiazolylmethyl, pyridylmethyl, each of which is optionally mono- to trisubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro or represent the groups

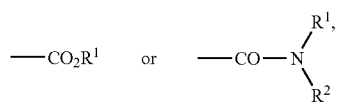

$Y^2$, $Y^4$, $Y^6$ independently of one another represent hydrogen or $C_1$–$C_4$-alkyl, $Y^5$ represents hydrogen, represents optionally fluorine-substituted $C_1$–$C_4$-alkyl or represents phenyl which is optionally mono- to trisubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano, or $Y^4$ and $Y^5$ furthermore together with the carbon atoms to which they are attached represent a 5- or 6-membered saturated or unsaturated cycle which may be interrupted by a heteroatom from the group consisting of N, O, S and which may optionally be mono- or disubstituted by fluorine, chlorine, bromine, methyl, tert-butyl, methoxy, trifluoromethyl, trifluoromethoxy, cyano or nitro, or $Y^1$ and $Y^2$ together with the carbon atom to which they are attached represent a $C_4$–$C_6$-cycloalkyl ring, Z represents hydrogen, represents in each case optionally fluorine- and/or chlorine-substituted $C_1$–$C_6$-alkyl, cyano-C—$C_3$-alkyl, $C_3$–$C_6$-alkenyl, $C_3$–$C_8$alkinyl, $C_3$–$C_6$-cycloalkyl, $C_3$–$C_6$-cycloalkyl-$C_1$–$C_2$-alkyl, $C_1$–$C_4$-alkoxy-$C_1$–$C_2$alkyl, $C_1$–$C_4$-halogeno-$C_1$–$C_2$-alkyl, represents phenoxy-$C_1$–$C_2$-alkyl, phenyl-$C_1$–$C_2$-alkyloxy-$C_1$–$C_2$-alkyl, phenylthio-$C_1$–$C_2$-alkyl, phenyl-$C_1$–$C_2$-alkylthio-$C_1$–$C_2$-alkyl, phenyl-$C_1$–$C_2$-alkyl, phenyl, pyridyl-$C_1$–$C_2$-alkyl, thiazolyl-$C_1$–$C_2$-alkyl, each of which is optionally mono- to trisubstituted by fluorine, chlorine, bromine, $C_1$–$C_4$-alkyl, C—$C_4$-alkoxy, $C_1$–$C_2$-halogenoalkyl, $C_1$–$C_2$-halogenoalkoxy, nitro or cyano or represents the groups

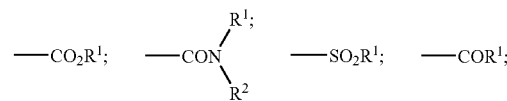

or cyano, where
p represents 0 to 2,
$R^1$ represents hydrogen (but not in the radicals —$CO_2R^1$ and —$SO_2R^1$), represents in each case optionally fluorine- and/or chlorine-substituted $C_1$–$C_6$-alkyl, $C_3$–$C_6$-alkenyl, $C_3$–$C_4$-alkinyl, represents in each case optionally fluorine-, chlorine-, $C_1$–$C_2$-alkyl-, $C_1$–$C_2$-alkoxy-substituted $C_3$–$C_6$-cycloalkyl or represents phenyl or benzyl, each of which is optionally mono- or disubstituted by fluorine, chlorine, bromine, $C_1$–$C_4$-alkyl, C—$C_4$-alkoxy, $C_1$–$C_2$-halogenoalkyl, $C_1$–$C_2$-halogenoalkoxy, cyano or nitro, $R^1$ represents hydrogen, represents in each case optionally fluorine- and/or chlorine-substituted $C_1$–$C_4$-alkyl, $C_3$–$C_4$-alkenyl, $C_3$–$C_4$-alkinyl, $C_1$–$C_4$-alkoxy, $C_3$–$C_4$-alkenyloxy or represents phenyl, benzyl, benzyloxy, each of which is optionally mono- or disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, or $R^1$, $R^2$ furthermore together with the nitrogen atom to which they are attached may represent an optionally $C_1$–$C_2$-alkyl-substituted five- or six-membered cycle in which optionally one methylene group may be replaced by oxygen, and $R^5$ represents hydrogen, methyl or ethyl,
$R^7$ represents C—$C_6$-alkyl, $C_2$–$C_6$-alkenyl, $C_3$–$C_6$-alkinyl, $C_1$–$C_6$-alkoxy, $C_1$–$C_4$-alkoxy-C—$C_2$-alkyl, $C_1$–$C_4$-alkylthio-$C_1$–$C_2$-alkyl, each of which is optionally substituted by fluorine and/or chlorine, represents $C_3$–$C_6$-cycloalkyl or $C_3$–$C_6$-cycloalkoxy in which optionally one methylene group may be replaced by oxygen and which are in each case optionally substituted by fluorine, chlorine, $C_1$–$C_2$-alky and/or $C_1$–$C_2$-alkoxy, represents phenyl, phenoxy, benzyloxy, thienyl, furanyl, pyridyl, pyrimidyl, thiazolyl, pyrazolyl or phenyl-$C_1$–$C_2$-alkyl, each of which is optionally mono- or disubstituted by fluorine, chlorine, bromine, $C_1$–$C_4$-alkyl, $C_1$–$C_4$-alkoxy, trifluoromethyl, difluoromethoxy, trifluoromethoxy, cyano or nitro or, in the case of the radicals a) and c) mentioned under Ar, also represents a group

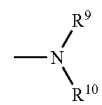

or, for the radical g), also represents hydroxyl,
$R^8$ represents hydrogen,
$R^9$ represents hydrogen, represents $C_1$–$C_6$-alkyl, $C_3$–$C_6$-alkenyl, $C_3$–$C_6$-alkinyl, $C_1$–$C_6$-alkoxy, $C_3$–$C_6$-cycloalkyl, in which optionally one methylene group may be replaced by oxygen and each of which is optionally substituted by fluorine and/or chlorine, represents phenyl or phenyl-$C_1$–$C_2$-alkyl, each of which is optionally mono- or disubstituted by fluorine, chlorine, bromine, $C_1$–$C_4$-alkyl, $C_1$–$C_4$-alkoxy, trifluoromethyl, difluoromethoxy, trifluoromethoxy, cyano or nitro, $R^{10}$ represents hydrogen or $C_1$–$C_4$-alkyl, or $R^9$, $R^{10}$ furthermore together with the nitrogen atom to which they are attached represent an optionally $C_1$–$C_2$-alkyl-substituted five- or six-membered cycle in which optionally one methylene group may be replaced by oxygen, and m represents 0 or 1.

4. A compound according to claim 1, wherein

K represents oxygen or sulphur,

Ar represents $Ar^1$, where $Ar^1$ represents substituted phenyl, thienyl, pyrimidyl, furanyl or pyridyl, each of which is optionally mono- to trisubstituted by fluorine, chlorine, bromine, methyl, ethyl, propyl, i-propyl, s-, n-, i- or t-butyl, methoxy, ethoxy, propoxy, i-propoxy, s-, n-, i- or t-butoxy, alkyloxy, methallyloxy, 2-butenyloxy, propargyloxy, 2-butinyloxy, methylthio, ethylthio, methylsulphinyl, ethylsulphinyl, methylsulphonyl, ethylsulphonyl, trifluoromethyl, difluoromethoxy, trifluoromethoxy, methylenedioxy, difluoromethylenedioxy, tetrafluoroethylenedioxy, difluoromethylthio, trifluoromethylthio, trifluoromethylsulphinyl, trifluoromethylsulphonyl, hydroxyl, mercapto, nitro, cyano, amino, or by one of the following groups a) 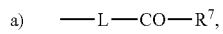 —L—CO—$R^7$, b) 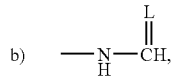

c) 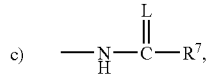

d) $NHSO_2R^7$, e) 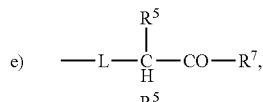

f) 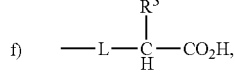

g) 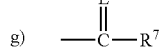

or represents $Ar^2$, where $Ar^2$ represents $Ar^1$ which is additionally substituted by phenyl, pyridyl, thienyl, tetrazolyl, triazolyl, benzyloxy, benzylthio, thiazolylmethyloxy, pyridylmethyloxy, pyrimidylmethyloxy, thiazolylmethylthio, pyridylmethylthio, phenoxy or phenylthio, where these substituents for their part are optionally mono- or disubstituted by fluorine, chlorine, bromine, methyl, ethyl, n- or i-propyl, s-, n-, i- or t-butyl, methoxy, ethoxy, i-propoxy, s-, n- or t-butoxy, trifluoromethyl, trifluoromethoxy, nitro or cyano, and L represents oxygen or sulphur, V represents oxygen, X represents

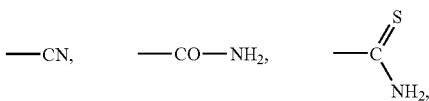

$Y^1$ and $Y^3$ independently of one another represent hydrogen, methyl, ethyl, propyl, iso-propyl, butyl, iso-butyl, sec-butyl, tert-butyl, represent phenyl or benzyl, each of which is optionally mono- to trisubstituted by fluorine, chlorine, bromine, methyl, methoxy, trifluoromethyl, difluoromethoxy or trifluoromethoxy, $Y^2$ 4, $Y^6$ independently of one another represent hydrogen, methyl or ethyl, $Y^5$ represents hydrogen, methyl, ethyl, propyl, i-propyl or represents phenyl which is optionally mono- or disubstituted by fluorine, chlorine, bromine, methyl, ethyl, i-propyl, tert-butyl, methoxy, ethoxy, i-propoxy, tert-butoxy, trifluoromethyl or trifluoromethoxy, or $Y^4$ and $Y^5$ together with the carbon atoms to which they are attached represent a six-membered unsaturated cycle which may optionally be monosubstituted by fluorine, chlorine, bromine, methyl, methoxy, trifluoromethyl, trifluoromethoxy, cyano or nitro, or $Y^1$ and $Y^2$ together with the carbon atom to which they are attached represent a cyclobutyl radical, Z represents hydrogen, methyl, ethyl, allyl, propargyl, cyclopropyl, cyclopentyl, cyclohexyl, cyclopropylmethyl, cyclopentylmethyl, cyclohexylmethyl, methoxymethyl, ethoxymethyl, represents phenyl, benzyl, pyridylmethyl, thiazolylmethyl, each of which is optionally mono- or disubstituted by fluorine, chlorine, bromine, methyl, methoxy, trifluoromethyl or trifluoromethoxy, cyano or nitro or represents the groups

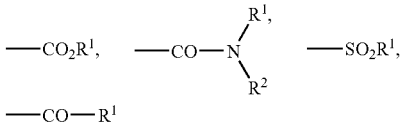

or cyano, where $R^x$ represents hydrogen (but not in the radicals —$CO_2R^1$ and —$SO_2R^1$), methyl, ethyl, propyl, isopropyl, n-, s-, i- or t-butyl, allyl, propargyl, cyclopropyl, cyclopentyl, cyclohexyl, represents phenyl or benzyl, each of which is optionally mono- or disubstituted by fluorine, chlorine, bromine, methyl, methoxy, trifluoromethyl, trifluoromethoxy, cyano or nitro, $R^2$ represents hydrogen, methyl, ethyl, propyl, isopropyl, allyl, propargyl, methoxy, ethoxy, alkyloxy or represents benzyloxy which is optionally mono- or disubstituted by fluorine, chlorine, bromine, methyl, methoxy, trifluoromethyl, trifluoromethoxy, cyano or nitro, or $R^1$, $R^2$ together with the nitrogen atom to which they are attached may represent a pyrrolidine, thiazine, piperidine or morpholine radical, $R^5$ represents hydrogen, methyl or ethyl, $R^7$ represents methyl, ethyl, propyl, isopropyl, n-, s-, i- or t-butyl, vinyl, trifluoromethyl, methoxy, ethoxy, propoxy, isopropoxy, n-, s-, i- or t-butyloxy, cyclopropyl, cyclopentyl, cyclohexyl, cyclopentyloxy, cyclohexyloxy, represents phenyl, pyridyl or benzyl, each of which is optionally mono- or disubstituted by fluorine, chlorine, bromine, methyl, n-, s-, i- or t-butyl, methoxy, trifluoromethyl, trifluoromethoxy, cyano or nitro or, in the case of the radicals a) and c) mentioned under Ar, also represents a group

or, for the radical g), also represents hydroxyl, $R^9$ represents hydrogen, methyl, ethyl, propyl, isopropyl, n-, s-, i- or t-butyl, cyclopropyl, cyclopentyl, cyclohexyl, represents phenyl which is optionally mono- or disubstituted by fluorine, chlorine, bromine, methyl, methoxy, trifluoromethyl, trifluoromethoxy, cyano or nitro, $R^{10}$ represents hydrogen, methyl or ethyl, $R^9$, $R^{10}$ together with the nitrogen atom to which they are attached represent a pyrrolidine, piperidine or morpholine radical, and m represents 1.

5. A compound according to claim 1, wherein

Ar represents $Ar^1$, where $Ar^x$ represents substituted phenyl, thienyl, pyrimidyl or pyridyl, each of which is optionally mono- to trisubstituted by fluorine, chlorine, bromine, methyl, ethyl, propyl, isopropyl, n-, s-, i- or t-butyl, methoxy, ethoxy, propoxy, isopropoxy, n-, s-, i- or t-butoxy, allyloxy, methallyloxy, 2-butenyloxy, propargyloxy, 2-butinyloxy, methylthio, ethylthio, methylsulphinyl, ethylsulphinyl, methylsulphonyl, ethylsulphonyl, trifluoromethyl, difluoromethoxy, trifluoromethoxy, methylenedioxy, difluoromethylenedioxy, tetrafluoroethylenedioxy, difluoromethylthio, trifluoromethylthio, trifluoromethylsulphinyl, trifluoromethylsulphonyl, hydroxyl, nitro, mercapto, cyano, amino, or represents $Ar^2$, where $Ar^2$ represents $Ar^1$ which is additionally substituted by phenyl, benzyloxy or phenoxy, where these substituents for their part are optionally mono- or disubstituted by fluorine, chlorine, bromine, methyl, ethyl, isopropyl, n-, s-, i- f or t-butyl, methoxy, ethoxy, isopropoxy, n-, s-, i- or t-butoxy, trifluoromethyl, trifluoromethoxy, nitro or cyano, K represents oxygen or sulphur, V represents oxygen, X represents CN, $Y^1$ and $Y^3$ independently of one another represent hydrogen, methyl, ethyl or propyl, Z represents hydrogen or methyl, m represents 1, and $Y^2$, $Y^4$, $Y^5$, $Y^6$ independently of one another represent hydrogen, methyl or ethyl.

6. A process for preparing a compound according to claim 1, selected from the group consisting of processes (A), (B), (C), (D), (E), (F) and (G), wherein (A) in said process (A), K represents oxygen and Z represents hydrogen, and said process (A) comprises the step of reacting a compound of the Formula (II),

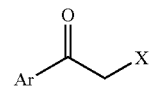

wherein

Ar and X are as defined in claim 1, with a compound of the Formula (III),

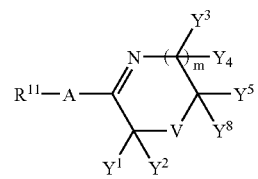

wherein

V, $Y^1$, $Y^2$, $Y^3$, $Y^4$, $Y^5$, $Y^6$ and m are as defined in claim 1, and A represents O or $S(O)_q$, where q represents 0 or 2, and $R^{11}$ represents alkyl, in particular $C_1$–$C_6$-alkyl, or benzyl, optionally in the presence of a diluent and optionally in the presence of a base or an acid and/or a metal compound of the Formula (IIIa), $Me(Q)_2$ (IIIa)

wherein

Me represents a divalent transition metal atom, optionally nickel, and

Q represents a chelate ligand, optionally a bidentate chelate ligand, optionally acetylacetonate, or (B) in said process (B), K represents oxygen and Z represents hydrogen, and said process (B) comprises the steps of reacting a compound of the Formula (IV),

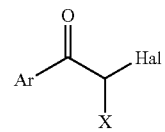

wherein

Ar and X are as defined in claim 1 and

Hal represents halogen, with a compound of the Formula (V),

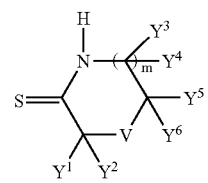

wherein

V, $Y^1$, $Y^2$, $Y^3$, $Y^1$, $Y^5$, $Y^6$ and m are as defined in claim 1 optionally in the presence of a diluent, to give a compound of the Formula (VI), (VI)

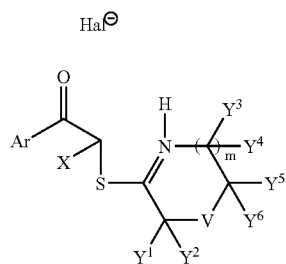

wherein

V, Ar, X, $Y^1$, $Y^2$, $Y^3$, $Y^4$, $Y^5$, $Y^6$ and m are as defined claim 1 and, reacting said compound of the Formula (VI) optionally in the presence of a base and optionally in the presence of a trivalent phosphorus compound with elimination of sulphur and hydrogen halide, to give a compound according to claim 1 in which K represents oxygen and Z represents hydrogen, or (C) in said process (C), K represents oxygen but Z does not represent hydrogen, and said process (C) comprises the steps of reacting a compound of the Formula (VII), (VII)

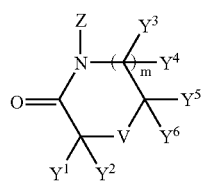

wherein

V, Z, $Y^1$, $Y^2$, $Y^3$, $Y^4$, $Y^5$, $Y^6$ and m are as defined in claim 1 and Z does not represent hydrogen, with a halogenating agent, wherein said halogenating agent is optionally selected from the group consisting of phosgene, diphosgene, triphosgene, and combinations thereof, optionally in the presence of a diluent, to give a compound of the Formula (VIII), (VIII)

wherein

V, Z, $Y^1$, $Y^2$, $Y^3$, $Y^4$, $Y^5$, $Y^6$ and m are as defined in claim 1 and Z does not represent hydrogen and

Hal represents halogen, and reacting said compound of the Formula (VIII) with a compound of the Formula (II), (II)

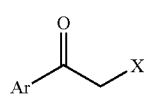

wherein

Ar, X are as defined in claim 1 optionally in the presence of a diluent and optionally in the presence of an acid acceptor, or (D) in said process (D), K represents oxygen but Z does not represent hydrogen, and said process (D) comprises the step of reacting a compound of the Formula (Ia), (Ia)

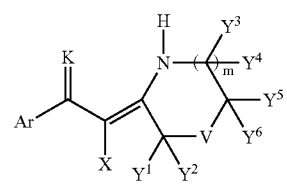

wherein

Ar, V, X, $Y^1$, $Y^2$, $Y^3$, $Y^4$, $Y^5$, $Y^6$ and m are as defined in claim 1

K represents oxygen, with a member selected from the group consisting of an alkylating agent, an acylating agent, a sulphonylating agent and a condensing agent of the Formula (IX),

Z-G (IX)

wherein

G represents a leaving group, optionally in the presence of a diluent and optionally in the presence of a base, or (E) in said process (E), K represents oxygen, and said process (E) comprises the step of reacting a compound of the Formula ($I^1$), (II)

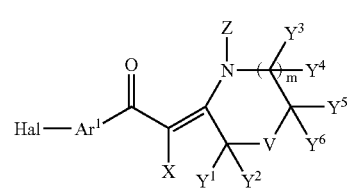

wherein $Ar^1$ is defined in claim 2 and, V, X, $Y^1$, $Y^2$, $Y^3$, $Y^4$, $Y^6$, Z and m are as defined in claim 1 and Hal represents halogen, optionally bromine, with a boronic acid of the Formula (X), (X)

$Ar^{2'}$—$B(OH)_2$ wherein $Ar^{2'}$ represents the substituents defined in claim 2 under $Ar^2$ as additional substituents for $Ar^1$, in the presence of a solvent, optionally in the presence of a base and a noble metal complex, said noble metal complex optionally being a palladium complex, or (F) in said process (F), K represents sulphur, said process (F) comprising the step of reacting a compound of the Formula (1), (I)

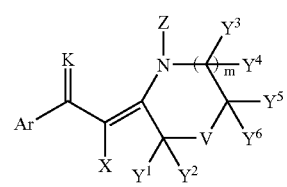

wherein
Ar, Z, V, X, $Y^1$, $Y^2$, $Y^3$, $Y^4$, $Y^5$, $Y^6$ and m are as defined in claim 1 and
K represents oxygen, with
a sulphurizing agent in the presence of a diluent, or
(G) in said process (G), V represents $S(O)_n$ and n represents 1 or 2,
said process (G) comprising the step of oxidizing a compound of the Formula (I),

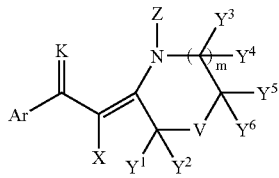

wherein
Ar, Z, K, X, $Y^1$, $Y^2$, $Y^3$, $Y^4$, $Y^5$, $Y^6$ and m are as defined in claim 1 and V represents a sulphur atom,
in the presence of a peracid or hydrogen peroxide in the presence of a molybdate or a tungstate.

7. A method for controlling undesirable vegetation and/or animal pests, comprising the step of allowing an effective amount of at least one compound according to claim 1 to act on a member selected from the group consisting of an undesirable plant, an animal pest, a habitat of said undesirable plant, a habitat of said animal pest and combinations thereof.

8. A composition, comprising a compound according to claim 1 and one or more extenders and/or one or more surfactants.

9. The composition of claim 8, wherein said composition is a member selected from the group consisting of an herbicidal composition, an acaricidal composition, and insecticidal composition and combinations thereof.

* * * * *